US010611829B2

(12) United States Patent
Kwakkenbos et al.

(10) Patent No.: US 10,611,829 B2
(45) Date of Patent: Apr. 7, 2020

(54) MEANS AND METHODS FOR PRODUCING STABLE ANTIBODIES

(71) Applicant: AIMM Therapeutics B.V., Amsterdam Zuidoost (NL)

(72) Inventors: Mark Jeroen Kwakkenbos, Amsterdam Zuidoost (NL); Koen Wagner, Amsterdam Zuidoost (NL); Adrianus Quirinus Bakker, Amsterdam Zuidoost (NL)

(73) Assignee: AIMM THERAPEUTICS B.V., Amsterdam Zuidoost (NL)

( * ) Notice: Subject to any disclaimer, the term of this patent is extended or adjusted under 35 U.S.C. 154(b) by 128 days.

(21) Appl. No.: 15/113,563

(22) PCT Filed: Jan. 30, 2015

(86) PCT No.: PCT/NL2015/050054

§ 371 (c)(1),
(2) Date: Jul. 22, 2016

(87) PCT Pub. No.: WO2015/115892

PCT Pub. Date: Aug. 6, 2015

(65) Prior Publication Data

US 2017/0008952 A1 Jan. 12, 2017

(30) Foreign Application Priority Data

Jan. 31, 2014 (EP) .................................... 14153480

(51) Int. Cl.

*C12N 5/00* (2006.01)
*C07K 16/10* (2006.01)
*C07K 16/00* (2006.01)
*C12Q 1/6869* (2018.01)

(52) U.S. Cl.

CPC .......... *C07K 16/1018* (2013.01); *C07K 16/00* (2013.01); *C12Q 1/6869* (2013.01); *C07K 2317/14* (2013.01); *C07K 2317/21* (2013.01); *C07K 2317/33* (2013.01); *C07K 2317/76* (2013.01); *C07K 2317/92* (2013.01); *C07K 2317/94* (2013.01)

(58) Field of Classification Search

None
See application file for complete search history.

(56) References Cited

U.S. PATENT DOCUMENTS

| | | | |
|---|---|---|---|
| 4,997,764 | A | 3/1991 | Dalla Favera |
| 5,684,147 | A | 11/1997 | Agrawal et al. |
| 5,849,900 | A | 12/1998 | Moelling |
| 5,866,757 | A | 2/1999 | Reisner |
| 6,001,558 | A | 12/1999 | Backus et al. |
| 7,378,276 | B2 | 5/2008 | Ettinger et al. |
| 7,964,406 | B2 | 6/2011 | Spits et al. |
| 8,247,228 | B2 | 8/2012 | Ettinger et al. |
| 2003/0099613 | A1 | 5/2003 | Berkhout et al. |
| 2003/0152559 | A1 | 8/2003 | Yang et al. |
| 2003/0158131 | A1 | 8/2003 | Aldovini |
| 2005/0009180 | A1 | 1/2005 | Yang et al. |
| 2005/0238626 | A1 | 10/2005 | Yang et al. |
| 2008/0274991 | A1 | 11/2008 | Berkhout et al. |
| 2008/0293068 | A1 | 11/2008 | Tsien et al. |
| 2008/0305076 | A1 | 12/2008 | Ettinger et al. |
| 2009/0093024 | A1 | 4/2009 | Bowers et al. |
| 2009/0217403 | A1 | 8/2009 | Spits |
| 2010/0093038 | A1 | 4/2010 | Spits |
| 2010/0113745 | A1 | 5/2010 | Spits et al. |
| 2010/0239593 | A1 | 9/2010 | Spits et al. |
| 2011/0020323 | A1 | 1/2011 | Beaumont et al. |
| 2012/0070446 | A1 | 3/2012 | Beaumont et al. |
| 2012/0151613 | A1 | 6/2012 | Wang et al. |

FOREIGN PATENT DOCUMENTS

| | | | |
|---|---|---|---|
| EP | 1627563 | | 2/2006 |
| EP | 1860120 | A1 | 11/2007 |
| EP | 1997830 | A1 | 12/2008 |
| GB | 2398783 | A | 9/2004 |
| JP | 2003012698 | A | 1/2003 |
| JP | 2007510666 | | 4/2007 |
| JP | 2008539794 | | 11/2008 |
| JP | 2010528601 | | 8/2010 |
| WO | 1989008146 | | 9/1989 |
| WO | 1994017086 | A1 | 1/1994 |
| WO | 1994008004 | | 4/1994 |
| WO | 1994027426 | A1 | 12/1994 |
| WO | 1995006409 | | 3/1995 |
| WO | 1996001313 | | 1/1996 |
| WO | 1996018413 | A1 | 6/1996 |
| WO | 2001018185 | A1 | 3/2001 |
| WO | 2001020013 | A2 | 3/2001 |
| WO | 2003050262 | A2 | 6/2003 |
| WO | 2003052083 | A2 | 6/2003 |

(Continued)

OTHER PUBLICATIONS

He, Feng, et al.; High Throughput Thermostability Screening of Monoclonal Antibody Formulations; Journal of Pharmaceutical Sciences, vol. 99, No. 4, Apr. 2010, pp. 1707-1720.
Dimitrov, Jordan D., et al.; Thermodynamic stability contributes to immunoglobulin specifity; CellPress—Trends in Biochemical Sciences, May 2014, vol. 39, No. 5, pp. 221-226 (XP-55119616).
Klein, Florian, et al.; Somatic Mutations of the Immunoglobulin Framework Are Generally Required for Broad and Potent HIV-1 Neutralization; Cell 153, Mar. 28, 2013, pp. 126-138 (XP-55119651 ).
Kwakkenbos, Mark J., et al.; Genetic manipulation of B cells for the isolation of rare thereapeutic antibodies from the human repertoire; Methods, 65 (2014) pp. 38-43 (XP-002719156).
McConnell, Audrey D., et al.; An intergrated approach to extreme thermostabilization and affinity maturation of an antibody; Protein Engineering, Design & Selection, 2012, pp. 1-13 (XP-55119708).

(Continued)

*Primary Examiner* — Michail A Belyavskyi
(74) *Attorney, Agent, or Firm* — Gianna J. Arnold; Saul Ewing Arnstein & Lehr LLP

(57) ABSTRACT

The invention provides means and methods for selecting and producing stable antibodies against an antigen of interest, using stable ex vivo B cell cultures.

10 Claims, 9 Drawing Sheets

(56) References Cited

FOREIGN PATENT DOCUMENTS

| | | | |
|---|---|---|---|
| WO | 2003068819 | A1 | 8/2003 |
| WO | 2003070193 | A2 | 8/2003 |
| WO | 2003079757 | A2 | 10/2003 |
| WO | 2004083249 | A2 | 9/2004 |
| WO | 2005052139 | A2 | 6/2005 |
| WO | 2005052164 | A1 | 6/2005 |
| WO | 2005044306 | A2 | 9/2005 |
| WO | 2005102383 | A1 | 11/2005 |
| WO | 2006016808 | A2 | 2/2006 |
| WO | 2006085518 | A1 | 8/2006 |
| WO | 2005123923 | A2 | 12/2006 |
| WO | 2006132524 | A1 | 12/2006 |
| WO | 2007058527 | A2 | 5/2007 |
| WO | 2007067032 | A1 | 6/2007 |
| WO | 2007067046 | A1 | 6/2007 |
| WO | 2008147196 | A2 | 12/2008 |
| WO | 2011008093 | A1 | 1/2011 |
| WO | 2011043643 | A1 | 4/2011 |
| WO | 2011008092 | A4 | 7/2011 |
| WO | 2012072814 | A1 | 6/2012 |
| WO | 2013081463 | A2 | 6/2013 |
| WO | 2013109279 | A2 | 7/2013 |
| WO | 2014008218 | A1 | 1/2014 |

OTHER PUBLICATIONS

Wang, Feng, et al.; Somatic hypermutation maintains anitbody thermodynamic stability during affinity maturation; PNAS, Mar. 12, 2013, vol. 110, No. 11, pp. 4261-4266 (XP-55119293).

Shapiro-Shelef, et al., Blimp-1 is required for maintenance of long-lived plasma cells in the bone marrow, The Journal of Experimental Medicine, Dec. 5, 2005, pp. 1471-76, vol. 202, No. 11.

Shen Chun-Pyn, et al., B-cell-specific DNA binding by an E47 homodimer, Molecular and Cellular Biology, 1995, pp. 4518-4524, vol. 15, No. 8.

Solvason, et al., Transgene Expression of bcl-xL Permits Anti-immunoglobulin (Ig-induced Proliferation in xid B Cells, J. Exp. Med., 1998, pp. 1081-1091, vol. 187.

Shvarts, et al., A senescence rescue screen identifies BCL6 as an inhibitor of anti-proliferative pI9 ARF-p53 signaling, Genes and Development, Mar. 15, 2002, vol. 16, No. 6, pp. 681-686.

Stier, et al., Notchl activation increases hematopoietic stem cell self-renewal in vivo and favors lymphoid over myeloid lineage outcome, Blood, vol. 99, No. 7, Apr. 1, 2002, pp. 2369-2378, XP002317904, ISSN: 006-4971, p. 2375, left-hand column.

Tan, et al., Zinc-finger Protein-Targeted Gene Fegulation: Genomewide Single-Gene Specificity, Proceedings of the National Academy of Sciences of the United States of America, Oct. 14, 2003, vol. 100, No. 21, pp. 11997-12002.

Tosato, et al., Identification of Interleukin-6 as an Autocrine Growth Factor for Epstein-Barr Virus-Immortalized B Cells, Journal of Virology, Jun. 1990, pp. 3033-3041, vol. 64, No. 6.

Toyama, et al., Memory B Cells Without Somatic Hypermutation Are Generated From Bcl6—Deficient B Cells, Immunity, Sep. 1, 2002, pp. 329-339, vol. 17, No. 3, Cell Press, US.

Traggiai, et al., Abstract; Development of a human adaptive immune system in cord blood cell-transplanted mice; Science (Washington, DC) vol. 304, No. 5667, Apr. 2, 2004, pp. 104-107, XP002356076, ISSN: 0036-8075, the whole document.

Traggiai, et al., Abstract; An efficient method to make human monoclonal antibodies from memory B cells: potent neutralization of SARS conoranavirus, Nature Medicine, Aug. 2004, pp. 871-875, vol. 10, No. 8.

Turner, et al., Blimp-1, A Novel Zinc Finger-Containing Protein That Can Drive the Maturation of B Lymphocytes into Immunoglobulin-Secreting Cells, Cell, Apr. 22, 1994, pp. 297-306, vol. 77.

Urlinger, et al., Exploring the sequence space for the tetracycline-dependent transcriptional activators: novel mutations yield expanded range and sensitivity, Proceedings of the National Academy of Sciences of USA, pp. 7963-7968, Jul. 5, 2000, vol. 97, No. 14, National Academy of Science, Washington, DC, US.

Van Regenmortel, Requirements for empirical immunogenicity trials, rather than structure-based design, for developing an effective HIV vaccine, Arch. Viral. (2012) 157: pp. 1-20.

Vickers, et al., Efficient reduction of target RNAs by small interfering RNA and RNase H-dependent antisense agents, 2003, The Journal of Biological Chemistry, vol. 278, pp. 7108-7118.

Weijer, et al., Intrathymic and extrathymic development of human plasmacytoid dendritic cell precursors in vivo; Blood, 2002; 99; 2752-2759.

Yamochi, et al. Adenovirus-mediated high expression of BCL-6 CV-1 cells induces apoptotic cell death accompanied by down-regulation of BCL-2 and BCL-XL, Oncogene, Jan. 14, 1999, pp. 487-494, vol. 18, No. 2.

Yang, et al. Generation of Functional antigen-specific T Cells in defined genetic backgrounds by retrovirus-mediated expression of TCR cDNAs in hematopoietic precursor cells, Proceedings of the National Academy of Sciences of USA, Apr. 30, 2002, pp. 6204-6209, vol. 99, No. 9, National Academy of Science, Washington, DC, US.

Zhang, et al., Up-Regulation of Bcl-XI Expression Protects CD40-Activated Human B Cells from Fas-Mediated Apoptosis, Cellular Immunology, 1996, pp. 149-154, vol. 173.

Zhou, et al. Improved single-chain transactivators of the Tet-On gene expression system, Biotechnology, 2007, p. 6, vol. 7.

Zhou, et al., Modification of the Tet-On regulatory system prevents the conditional-live HIV-1 variant from losing doxycycline-control, Retrovirology, 2006, p. 82, vol. 3.

Zhou, et al. Optimization of the Tet-On system for regulated gene expression through viral evolution, Gene Therapy, Oct. 2006, pp. 1382-1390, vol. 13, No. 39.

Zhou, et al., The genetic stability of a conditional live HIB-1 variant can be improved by mutations in the Tet-On regulatory system that restrain evolution, The Journal of Biological Chemistry, Jun. 23, 2006, pp. 17084-17091, vol. 281, No. 25.

Ahmad, et al., Mechanism of SMRT Corepressor Recruitment by the BCL6 BTB Domain, Molecular Cell, Dec. 2003, pp. 1551-1564, vol. 12.

Alajez, et al., Therapeutic potential of a tumor-specific, MHC-unrestricted T-cell receptor expressed on effector cells of the innate and the adaptive immune system through bone marrow transduction and immune reconstitution; Blood, Jun. 15, 2005, vol. 105, No. 12; pp. 4583-4589.

Barnett, et al., Determination of leucocyte antibody binding capacity (ABC): the need for standardization. Clin. Lab. Haem., 1998, vol. 20, pp. 155-164.

Becker, et al., Generation of Human Antigen-Specific Monoclonal IgM Antibodies Using Vaccinated “Human Immune System” Mice, PLOS One, Oct. 4, 2010, vol. 5, No. 10.

Boise, et al., bcl-x, a bcl-2-Related Gene That Functions as a Dominant Regulator of Apoptotic Cell Death, Cell, Aug. 27, 1983, pp. 597-608, vol. 74.

Buckland, Blimp1, BCL6, and B-Cell Fate, Nature Reviews Immunology. Sep. 2002, pp. 629-629, vol. 2.

Charbonneau, et al., Prolongation of murine hybridoma cell survival in stationary batch culture by Bcl-XI expression, Cytotechnology, 2000, pp. 131-139, vol. 34.

Chlewicki, et al., High-affinity, Peptide-specific T Cell Receptors can be Generated by Mutations in CDR1, CDR2 or CDR3; J. Mol. Biol.; 2005; vol. 346, pp. 223-239.

Clay, et al., Efficient Transfer of a Tumor Antigen-Reactive TCR to Human Peripheral Blood Lymphocytes Confers Anti-Tumor Reactivity, Journal of Immunology, 1999, pp. 507-513, vol. 163, The Williams and Wilkins Co. Baltimore, MD, US.

Clay, et al. Potential Use of T Cell Receptor Genes to Modify Hematopoietic Stem Cells for the Gene Therapy of Cancer, Pathology Oncology Research, 1999, pp. 3-15, vol. 5, No. 1, Budapest, Hungary.

Das, et al., Abstract, A Conditionally Replicating Virus as a Novel Approach Toward an HIV Vaccine, Methods in Enzymology, 2004, pp. 359-379, vol. 388, Academic Press, San Diego, US.

(56) References Cited

OTHER PUBLICATIONS

Das, et al., Viral evolution as a tool to improve the tetracycline-regulated gene expression system, The Journal of Biological Chemistry, Apr. 30, 2004, pp. 18776-18782, vol. 279, No. 18.
Epeldegui, et al., Infection of Human B Cells with Epstein-Barr Virus Results in the Expression of Somatic Hypermutation-Inducing Molecules and in the Accrual of Oncogene Mutations, Molecular Immunology, Feb. 1, 2007, vol. 44, No. 5, Pergamon, GB.
Gil, et al., Somatic Mutations and Activation-Induced Cytidine Deaminase (AID) Expression in Established Rheumatoid Factor-Producing Lymphoblastoid Cell Line, Molecular Immunology, Jan. 1, 2007, pp. 494-505, vol. 14, No. 4, Pergamon, GB.
Gimeno, et al. Monitoring the effect of gene silencing by RNA interference in human DC34<-/-> cells injected into newborn RAG2<-/-> |gammalc <-/-> mice: Functional inactivation of p53 in developing T cells, Blood Dec. 15, 2004 United States, vol. 104 No. 13, Dec. 15, 2004, pp. 3886-3893, XP002317351, ISSN: 0006-4971, the whole document.
Goldman, et al., Enhanced human cell engraftment in mice deficient in RAG2 and the common cytokine receptor gamma chain, British Journal of Haematology, Oxford, GB, vol. 103, No. 2, Nov. 1998, pp. 335-342, XP002249529; ISSN: 0007-1048, the whole document.
Gossen, et al., Abstract, Transcriptional Activation by Tetracyclines in Mammalian Cells, Science, Jun. 23, 1995, pp. 1766-1769, vol. 268, American Association for the Advancement of Science, US.
Grillot, et al., bcl-x Exhibits Regulated Expression During B Cell Development and Activation and Modulates Lymphocyte Survival in Transgenic Mice; The Journal of Experimental Medicine, vol. 183, Feb. 1996, pp. 381-391.
Jung, et al., Inducible Expression of Bcl-XL Restricts Apoptosis Resistance to the Antibody Secretion Phase in Hybridoma Cultures, Biotechnology and Bioengineering, pp. 180-187, vol. 79.
Kang, et al. Long-term expression of a T-cell receptor beta-chain gene in mice reconstituted with retrovirus-infected hematopoietic stem cells, Proc. Natl. Acad. Sci., Dec. 1990, pp. 9803-9807, vol. 87, National Academy of Science, Washington, DC, US.
Knodel, et al., Abstract, Blimp-1 over-expression abrogates IL-4- and CD40-mediated suppression of terminal B cell differentiation but arrests isotype switching, European Journal of Immunology, 2001, pp. 1972-1980, vol. 31, No. 7.
Knott, et al., Tetracycline-dependent Gene Regulation: Combinations of Transregulators Yield of a Variety of Expression Windows, Biotechniques, 2002, pp. 796-806, vol. 32, No. 4; Informa Life Sciences Publishing, Westborough, MA, US.
Kobayashi, et al., Abstract, Prevention of acute liver failure in rats with reversibly immortalized human hepatocytes; Science (Washington, DC), vol. 287, No. 5456, Feb. 18, 2000, pp. 258-1262, XP002159501, ISSN: 0036-8075.
Koff, HIV vaccine development: Challenges and opportunities towards solving teh HIV vaccine-neutralizing antibody problem; Vaccine vol. 30 (2012) pp. 4310-4315.
Kriangkum, et al., Impaired class switch recombination (CSR) in Waldenström macroglobulinemia (WM) despite apparently normal CSR machinery; Blood, 2006, v. 107, pp. 2920-2927.
Krueger, et al., Single-chain Tet Transregulators, Nucleic Acids Research Jun. 15, 2003, pp. 3050-3056, vol. 31, No. 12 Oxford University Press, Surrey, GB.
Kwakkenbos, et al., Generation of Stable Monoclonal Antibody-Producing B Cell Receptor-Positive Human Memory B Cells by Genetic Programming, Nature Medicine, Jan. 1, 2010, pp. 123-128; vol. 16, No. 1.
Kyba, et al., Enhanced hematopoietic differentiation of embryonic stem cells conditionally expressing Stat5, Whitehead Institute for Biomedical Research, pp. 1-12.
Lee, et al., Regulation of the Germinal Center Gene Program by Interferon (IFN) Regulatory Factor 8/IFN Consensus Sequence-Binding Protein, Journal of Experimental Medicine, Jan. 2006, pp. 63-72, vol. 203, No. 1.
Lin, et al., Blimp-1-Dependent Repression of Pax-5 is Required for Differentiation of B Cells to Immunoglobulin M-Secreting Plasma Cells, Molecular and Cellular Biology, Jul. 2002, pp. 4771-4780, vol. 22, No. 13.
Mathas, et al., Intrinsic inhibition of transcription factor E2A by HLH proteins ABF-1 and Id2 mediates reprogramming of neoplastic B cells in Hodgkin lymphoma, Nature Immunology, Feb. 2006, pp. 207-215, vol. 7, No. 2.
Muramatsu, et al., Class Switch Recombination and Hypermutation Require Activation-Induced Cytidine Deaminase (AID), a Potential RNA Editing Enzyme, Cell, Sep. 1, 2000, pp. 553-563, vol. 102, No. 5.
Mehta, et al., IL-21 induces the apoptosis of resting and activated primary B cells, Journal of Immunology, Apr. 15, 2003, pp. 4111-4118, vol. 170, No. 8, Hie Williams and Wilkins Co., Baltimore, MD, US.
Morrison, et al.,Vectors and Approaches for the Eukaryotic Expression of Antibodies and Anitbody Fusion Proteins, Antibody Engineering, 2nd ed., Chapter 9, pp. 267-293.
Mulloy, et al. Maintaining the self-renewal and differentiation potential of human CD34+ hematopoietic cells using a single genetic element, Blood, vol. 102, No. 13, Dec. 15, 2003, pp. 4369-4376, XP002317905, ISSN: 0006-4971, the whole document.
Ozaki, et al., Regulation of B cell differentiation and plasma cell generation by IL-21, a novel inducer of Blimp-1 and Bcl-6, Journal of Immunology, Nov. 1, 2004, pp. 5361-5371, vol. 173, No. 9.
Petrie, et al., T Cell Receptor Gene Recombination Patterns, and Mechanisms: Cell Death, Rescue, and T Cell Production, J Exp Med 1995, vol. 182, pp. 121-127.
Park, Hong-Jai, et al., Insights into the Role of Follicular Helper T Cells in Autoimmunity, Immune Network, vol. 14, No. 1: pp. 21-29, Feb. 2014.
Roughan, et al., The Intersection of Epstein-Barr Virus with the Germinal Center, Journal of Virology, Apr. 15, 2009, vol. 83, No. 8, pp. 3968-3976.
Reljic, et al., Suppression of Signal Transducer and Activator of Transcription 3-dependent B Lymphocyte Terminal Differentiation by BCL-6, J. Exp. Med., Dec. 18, 2000, vol. 192, pp. 1841-1847, Rockefeller University Press.
Ryvbal'skiy N.G., Serova M.A., Igantyeva G.A., Starcheus A.P. "Monoklonal'nyye antitela gibribomy" (translation: Monoclonal antibodies and hybridomas), Moskva, Vaskhnil, 1989, pp. 23-44. English summary is attached.
Salucci, et al., Tight control of gene expression by a helper-dependent adenovirus vector carrying the rtTA2S-M2 tetracycline transactivator and repressor systems, Gene Therapy, 2002, pp. 1415-1421, vol. 9, Macmillam Press Ltd., Basingstoke, GB.
Schaft, et al., Peptide fine specificity of anti-gylcoprotein 100 CTL is preserved following transfer of engineered TCRαβ genes into primary human T lymphocytes. The Journal of Immunology, 2003, vol. 170, pp. 2186-2194.
Scheeren, et al., STAT5 regulates the self-renewal capacity and differentiation of human memory B cells and controls Bcl-6 expression, Nature Immunology, 2005, vol. 6, pp. 303-313.
Schuringa, et al., Constitutive activation of STAT5A promotes human hematopoietic stem cell self-renewal and erythroid differentiation, Journal of Experimental Medicine, vol. 200, No. 5, Sep. 6, 2004, pp. 623-635.
Schuringa, et al., Enforced Activation of STAT5A Facilitates the Generation of Embryonic Stem-Derived Hematopoietic Stem Cells That Contribute to Hematopoiesis In Vivo, Stem Cells 2004, vol. 22, pp. 1191-1204.
Sciammas, et al., Modular Nature of Blimp-1 in the Regulation of Gene Expression during B Cell Maturation, The Journal of Immunology, 2004, pp. 5427-5440, vol. 172.
Shaffer, et al., Blimp-1 orchestrates plasma cell differentiation by extinguishing the mature B cell gene expression program, Immunity, Jul. 2002, pp. 51-62, vol. 17, No. 1.
Shaffer, A.L., et al., Lymphoid Malignancies: The Dark Side of B-Cell Differentiation, Nature Reviews, Immunology, vol. 2, pp. 1-13, Dec. 2002.

(56) References Cited

OTHER PUBLICATIONS

Shapiro-Shelef, et al., Blimp-1 is Required for the Formation of Immunoglobulin Secreting Plasma Cells and Pre-Plasma Memory B Cells, Immunity, Oct. 2003, pp. 607-620, vol. 19.
Diehl, Sean A., et al.; "STAT3-Mediated Up-Regulation of Blimp1 is Coordinated with BCL6 Down-Regulation to Control Human Plasma Cell Differentiation;" The Journal of Immunology, 2008, vol. 180, pp. 4805-4815.
Christopherson, Karen S., et al.; "Ecdysteroid-dependent regulation of genes in mammalian cells by a Drosophila ecdysone receptor and chimeric transactivators;" Proc. Natl. Acad. Sci. USA, Jul. 1992, vol. 89, pp. 6314-6318.
Chipuk, Jerry E., et al.; "How do BCL-2 proteins induce mitochondrial outer membrane permeabilization?;" Cell Press, Trends in Cell Biology; vol. 18, No. 4, pp. 157-164.
Banchereau, Jacques, et al.; "Long-Term Human B Cell Lines Dependent on Interleukin-4 and Antibody to CD40;" Sciences, Jan. 4, 1991, vol. 251, No. 4989, pp. 70-72.
Adams, Jerry M., et al.; "Bcl-2 regulated apoptosis: mechanism and therapeutic potential;" Sciencedirect, Current Opinion in Immunology; 2007, vol. 19, pp. 488-496.
Close, Pauline M., et al.; "Zonal Distribution of Immunoglobulin-Synthesizing Cells Within the Germinal Centre: An In Situ Hybridization and Immunohistochemical Study;" Journal of Pathology, 1990, vol. 162, pp. 209-216.
Liu, Yong-Jun, et al.; "Germinal center development;" Immunological Reviews, 1997, vol. 156, pp. 111-126.
Kinsella, Todd M., et al.; "Episomal Vectors Rapidly and Stably Produce High-Titer Recombinant Retrovirus;" Human Gene Therapy, Aug. 1, 1996, vol. 7; pp. 1405-1413.
Ye, Bihui H., et al.; "The BCL-6 proto-oncogene controls germinal-centre formation and Th2-type inflammation;" Nature Publishing Group, Jun. 16, 1997, vol. 16, pp. 161-170.
Zamore, Phillip D., et al.; "RNAi: Double-Stranded RNA Directs the ATP-Dependent Cleavage of mRNA at 21 to 23 Nucleotide Internals;" Cell, Mar. 31, 2000, vol. 101, pp. 25-33.
Ettinger, Rachel, et al.; "IL-21 Induces Differentiation of Human Naive and Memory B Cells into Antibody-Secreting Plasma Cells;" The Journal of Immunololgoy, 2005, vol. 175, pp. 7867-7879.
Johnson, Syd, et al.; "A Direct Comparison of the Activities of Two Humanized Respiratory Syncytial Virus Monoclonal Antibodies: MEDI-493 and RSHZ19;" The Journal of Infectious Disease, 1999, vol. 180, pp. 35-40.
Smit, Laura A., et al.; "Expression of Activation-induced Cytidine Deaminase is Confined to B-Cell Non-Hodgkin's Lymphomas of Germinal-Center Phenotype;" Cancer Research, Jul. 15, 2003, vol. 63, pp. 3894-3898.
Jung, Daniel, et al.; "Inducible Expression of Bcl-XL Restricts Apoptosis Resistance to the Antibody Secretion Phase in Hybridoma Cultures;" 2002 Wiley Periodicals Inc., pp. 180-187.
Liu, Xinqi, et al.; "The Structure of a Bcl-xL/Bim Fragment Complex: Implications for Bim Function;" Immunity, Sep. 2003, vol. 19, pp. 341-352.
Ning, Zhi-Qiang, et al.; "Distinct mechanisms for rescue from apoptosis in Ramos human B cells by signaling through CD40 and interleukin-4 receptor: role for inhibition of an early response gene;" Eur. J. Immunol., 1996, vol. 26, pp. 2356-2363.
Tey, Beng, et al.; "Effect of Bcl-2 Overexpression on Cell Cycle and Antibody Productivity in Chemostat Cultures of Myeloma NS0 Cells;" Journal of Bioscience and Bioengineering, 2005, vol. 100, No. 3, pp. 303-310.
Yoo, Esther M., et al.; "Myeloma expression systems;" Journal of Immunological Methods, 2002, vol. 261, pp. 1-20.
Baron, Udo, et al.; "Tet-Repressor-Based System for Regulated Gene Expression in Eukaryotic Cells: Principles and Advances;" Methods in Enzymology, vol. 327, pp. 401-421.
Guzman, Luz-Maria, et al.; "Tight Regulation, Modulation, and High-Level Expression by Vectors Containing the Arabinose PBAD Promoter;" Journal of Bacteriology, Jul. 1995, pp. 4121-4130.
Muramatsu, Masamichi, et al.; "Specific Expression of Activation-induced Cytidine Deaminase (AID), a Novel Member of the RNA-editing Deaminase Family in Germinal Center B Cells;" The Journal of Biological Chemistry, Jun. 25, 1999, vol. 274, No. 26, pp. 18470-18476.
Kee, Barbara L.; "E and ID proteins branch out;" Nature Reviews Immunology, Mar. 2009, vol. 9, pp. 175-184.
Kuo, Tracy C., et al.; "Repression of BCL-6 is required for the formation of human memory B cells in vitro;" The Journal of Experimental Medicine, Apr. 16, 2007, vol. 204, No. 4, pp. 819-830.
Lokate, Angelique M.C., et al.; "Biomolecular Interaction Monitoring of Autoantibodies by Scanning Surface Plasmon Resonance Microarray Imaging;" J. Am. Chem. Soc., 2007, vol. 129, pp. 14013-14018.
Malisan, Florence, et al.; "Interleukin-10 Induces Immunoglobulin G Isotype Switch Recombination in Human CD40-Activated Naive B Lymphocytes;" The Journal of Experimental Medicine, Mar. 1996, vol. 183, pp. 937-947.
Maurer, Ulrich, et al.; "Glycogen Synthase Kinase-3 Regulates Mitochondrial Outer Membrane Permeabilization and Apoptosis by Destabilization of MCL-1;" Molecular Cell, Mar. 17, 2006, vol. 21, pp. 749-760.
Ichikawa, H. Travis, et al.; "Structural Phylogenetic Analysis of Activation-Induced Deaminase Function;" The Journal of Immunology, 2006, vol. 177, pp. 355-361.
Peled, Jonathan U., et al.; "The Biochemistry of Somatic Hypermutation;" Annu. Rev. Immunol, 2008, vol. 26, pp. 481-511.
Gossen, Manfred, et al.; "Tight control of gene expression in mammalian cells by tetracycline-responsive promoters;" Proc. Natl. Acad. Sci. USA, Jun. 1992, vol. 89, pp. 5547-5551.
Rousset, Francoise, et al.; "Interleukin 10 is a potent growth and differentiation factor for activated human B lymphocytes;" Proc. Natl. Acad. Sci. USA, Mar. 1992, vol. 89, pp. 1890-1893.
Dadgostar, Hajir, et al.; "Cooperation of multiple signaling pathways in CD40-regulated gene expression in B lymphocytes;" PNAS, Feb. 5, 2002, vol. 99, No. 3, pp. 1497-1502.
Sidwell, Robert W., et al.; "Respiratory syncytial virus infections: Recent prospects for control;" Sciencedirect, Antiviral Research, 2006, vol. 71, pp. 379-390.
Spits, Hergen, et al.; "Id2 and Id3 Inhibit Development of CD34 Stem Cells into Predendritic Cell (Pre-DC)2 but Not into Pre-DC1: Evidence for a Lymphoid Origin of Pre-DC2;" J. Exp. Med., Dec. 18, 2000, vol. 192, No. 12, pp. 1775-1783.
Thompson, William W., et al.; "Mortality Associated With Influenza and Respiratory Syncytial Virus in the United States;" American Medical Association, Jan. 8, 2003, vol. 289, No. 2, pp. 179-186.
Hall, Caroline Breese, et al.; "The Burden of Respiratory Syncytial Virus Infection in Young Children;" The New England Journal of Medicine, Feb. 5, 2009, vol. 360, pp. 588-598.
Good, Kim L., et al.; "Kinetics of Human B Cell Behavior and Amplification of Proliferative Responses following Stimulation with IL-21;" The Journal of Immunology, 2006, vol. 177, pp. 5236-5247.
Ettinger, Rachel, et al.; IL-21 is a Pivotal Cytokine in the Induction of TCell-Dependent B Cell Activation, Differentiation and IG Secretion; Garn 2005 Novel Therapeutic Targets and Strategies, Section 107.
Garber, E., et al.; A broad range of Fab stabilities within a host of therapeutic IgGs; Biochemical and Biophysical Research Communications 355 (2007), pp. 751-757.

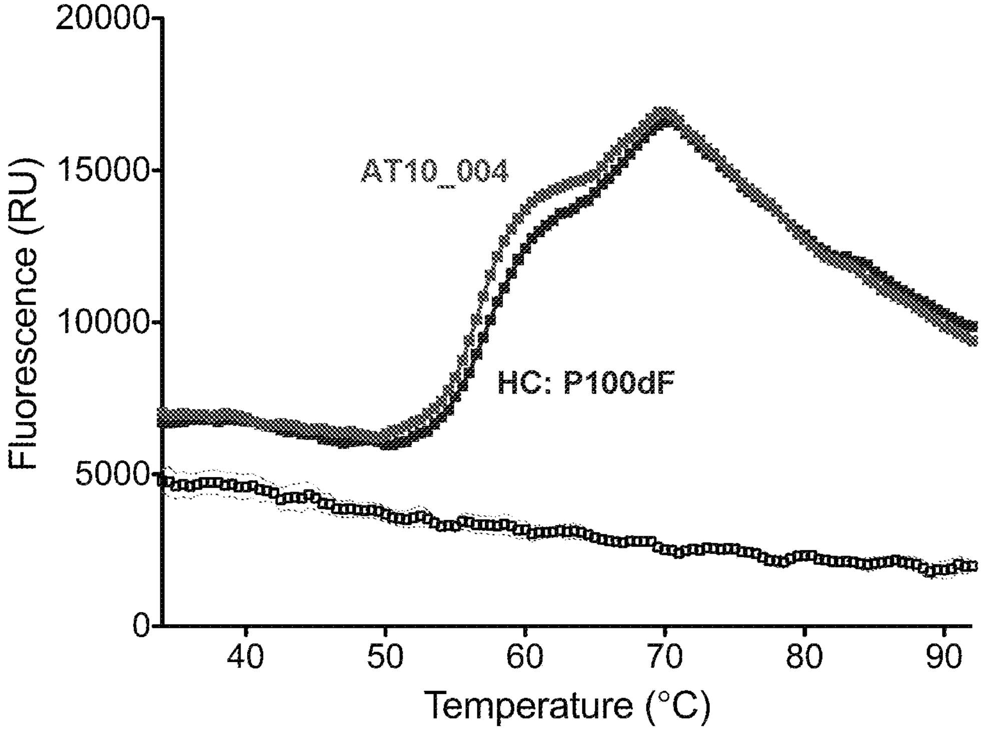
FIG. 3, Cont'd

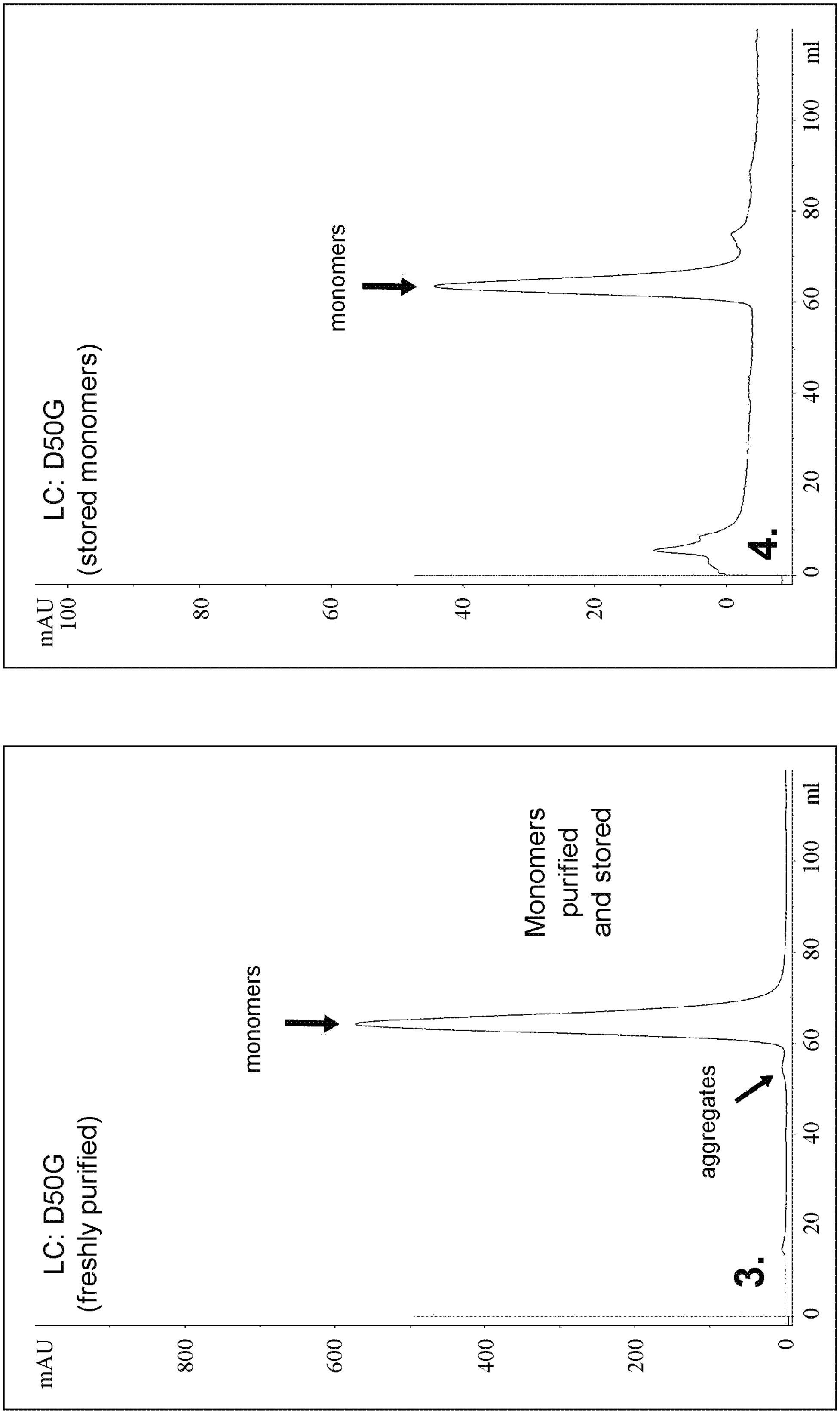
FIG. 4B, Cont'd

MEANS AND METHODS FOR PRODUCING STABLE ANTIBODIES

CROSS REFERENCE TO RELATED APPLICATIONS

This application claims the priority of PCT/NL2015/050054, filed on Jan. 30, 2015, which claims priority to EP Application No. 14153480.0, filed on Jan. 31, 2014, the entire contents of each of which are hereby incorporated in total by reference.

The invention relates to the fields of medicine, molecular biology and immunology. More specifically, the invention relates to the field of antibodies.

Ex vivo B cell cultures are important tools for producing antibodies, preferably monoclonal antibodies. Monoclonal antibodies (mAbs) represent multiple identical copies of a single antibody molecule, which copies bind to antigens with the same affinity and promote the same effector functions. Amongst the benefits of mAbs is their specificity for the same epitope on an antigen. This specificity confers certain clinical advantages on mAbs over more conventional treatments while offering patients an effective, well-tolerated therapy option with generally low side effects. Moreover mAbs are useful for biological and medical research.

A conventional approach for obtaining mAbs is hybridoma technology, wherein a B cell is fused with a myeloma cell in order to form hybrid antibody producing cell lines (hybridomas). However, hybridoma technology with human B cells has not been very successful because the resulting hybridomas are unstable. Meanwhile, an improved technology has been developed wherein ex vivo B cell cultures are produced with a prolonged replicative life span (WO 2007/067046). This technology involves human ex vivo cultures wherein BCL6, together with Blimp-1 and/or an anti-apoptotic nucleic acid, are expressed in the B cells. This improves the replicative life span of these B cells. Typically, human B cells are cultured in order to obtain human mAbs. Human mAbs are preferred for therapeutic applications in humans due to the lower immunogenicity as compared to antibodies of other species.

One of the problems faced when commercially producing antibodies, e.g. for pharmaceutical or research applications, is to obtain antibodies that are stable enough for instance for production in large quantities, for administration to patients and/or for long-term storage. Considerable effort is put in increasing the stability of in particular therapeutic antibodies. In the early phases of research and development of antibodies with a specificity and high affinity for an antigen of interest, stability is typically not a property that is taken into account. Instead, stability of antibodies is altered by introducing mutations in the encoding nucleic acid and testing the resulting antibodies for their stability once antibodies with the desired specificity and affinity are identified. Given the cost of producing these mutated antibodies and the time involved, alternative methods for obtaining stable antibodies are desired.

It is an object of the present invention to provide means and methods for selecting B cells capable of producing stable antibodies and for producing such stable antibodies, as well as for producing B cells capable of producing such stable antibodies. In particular, the method of the present invention allow for the selection of stable antibodies at an early stage in the development process.

The invention provides a method for producing a B cell, preferably a B cell culture, capable of producing antibody for an antigen of interest comprising:

a) selecting at least one B cell capable of producing antibody specific for said antigen of interest or at least one B cell capable of developing into a B cell capable of producing antibody specific for said antigen of interest;

b) inducing, enhancing and/or maintaining expression of BCL6 and inducing, enhancing and/or maintaining expression of an anti-apoptotic nucleic acid in said at least one B cell;

c) allowing expansion of said at least one B cell into a first B cell culture;

d) selecting at least one B cell from said first B cell culture with a binding avidity for said antigen of interest that is higher than the average binding avidity for said antigen of interest of B cells in said first B cell culture;

e) preferably allowing expansion of said at least one B cell selected in step d) into a second B cell culture;

f) determining the stability of antibodies produced by said at least one B cell selected in step d) or by said second B cell culture; and g) selecting at least one B cell capable of producing antibodies with a higher stability as compared to the average stability of antibodies produced by B cells of said first B cell culture. Preferably, said at least one B cell selected in step g) is expanded into a further B cell culture.

Further provided is a method for selecting from an ex vivo B cell culture at least one B cell capable of producing antibodies with a higher stability as compared to the average stability of antibodies produced by said ex vivo B cell culture, the method comprising:

a) providing an ex vivo B cell culture capable of producing antibody specific for an antigen of interest;

b) selecting at least one B cell from said ex vivo B cell culture with a binding avidity for said antigen of interest that is higher than the average binding avidity of B cells of said ex vivo B cell culture for said antigen of interest;

c) determining the stability of antibodies produced by said at least one B cell selected in step b); and d) selecting at least one B cell capable of producing antibodies with a higher stability as compared to the average stability of antibodies produced by B cells of said ex vivo B cell culture.

As used herein "specific for an antigen (of interest)" and "capable of specifically binding an antigen (of interest)" refer to the interaction between an antibody and its antigen, meaning that said antibody preferentially binds to said antigen over other antigens. Thus, although the antibody may non-specifically bind to other antigens, the affinity of said antibody for its antigen is significantly higher than the non-specific affinity of said antibody for any other antigens. A B cell capable of producing antibody specific for an antigen of interest is for instance obtained by isolation of memory B cells from peripheral blood, followed by staining with labelled antigen and isolation of antigen-bound B cells as described by Kwakkenbos et al. (Nature medicine, 16(1), 123-128. doi:10.1038/nm 2071; Methods 2013 doi:10.1016/j.ymeth.2013.07.002; patent application WO 2007/067046).

A method of the present invention involves determining the binding avidity of at least one B cell and determining the average binding avidity of B cells of the B cell culture from which the at least one B cell originates for an antigen of interest. Subsequently, a B cell is selected with a higher binding avidity than the average binding avidity of B cells of the B cell culture. As used herein the term "binding avidity" refers to the accumulated strength of all interactions contributing to the binding of a B cell to an antigen of interest. A factor that contributes to the binding of a B cell to an antibody of interest is the number of B cell receptors expressed on the cell surface of the B cell. Indeed, it was confirmed in WO 2012/072814 that when selected for binding capacity for a given antigen, B cells sorted for a relatively low binding capacity to an antigen did express less immunoglobulin on the surface of the B cells as compared to B cells sorted for higher binding. Nevertheless, when the B cells with higher antigen binding were cultured, they appeared to produce antibodies that had a higher affinity for the antigen as compared to antibody produced by the B cells with lower antigen binding. In WO 2012/072814 it was further surprisingly found that if such higher affinity B cell selected from the first population based on its antigen binding is expanded into a second population of B cells, the B cells in this second population retain the higher affinity of the selected B cell instead of returning to the average affinity of B cells in the first population as would be expected. Hence, affinity of secreted antibody for the antigen is also correlated with binding capacity of a B cell for a given antigen. In WO 2012/072814 it was therefore concluded that B cells that produce antibodies with a high affinity for an antigen of interest can be selected and further cultured while maintaining high affinity based on high antigen binding of the selected B cell to the antigen.

The present invention provides the insight that another factor that correlates with the binding avidity of a B cell for a specific antigen is the stability of antibody produced by said B cell. The present inventors surprisingly found that, in addition to a subset of the B cells selected for having a high binding avidity for an antigen that indeed produces antibodies with a high binding affinity for the antigen as described in WO 2012/072814, another subset of B cells selected for having a high binding avidity for the antigen produces antibodies that have a high stability. It was further found that the highly stable antibodies produced by this subset of B cells with a high binding avidity do not necessarily have a high affinity for the antigen. For instance, a subset of B cells with a high binding avidity for an antigen produces antibodies that are highly stable and that have an average affinity for the antigen; a second subset of B cells with a high binding avidity for an antigen produces antibodies that are highly stable and that have a high affinity for the antigen; a third subset of B cells with a high binding avidity for an antigen produces antibodies that have an average stability and a high affinity for the antigen; a fourth subset of B cells with a high binding avidity for an antigen produces antibodies that are instable but have a high affinity for the antigen; etc. The present invention for the first time establishes a correlation between the binding avidity of B cells for an antigen of interest and the stability of antibodies produced by these B cells. Further, the invention shows that spontaneous mutations in the genes encoding antibodies occur while the antibodies maintain their specificity and/or affinity for a specific antigen, for which a pre-selection can be made by determining the binding avidity of B cells producing the antibodies. Further, the invention for the first time describes the selection of stability of antibodies by determining the characteristics of B cells producing the antibodies.

Without being bound to any theory, it is believed that differences in the affinity of antibodies for an antigen of interest or differences in stability of antibodies within a population of monoclonal B cells may result from processes mediated by Activation Induced Cytidine Deaminase (AID). Antigen-activated naïve and memory B cells in the germinal centre undergo extensive proliferation, accompanied by somatic hypermutations (SHM) and class-switch recombination (CSR) of Ig genes mediated by AID. AID deaminates deoxycytidine residues in immunoglobulin genes, which triggers antibody diversification. The expression of AID in (a B cell which will develop into) an antibody producing B cell allows the generation of novel immunoglobulins that harbor mutations that were not present in the original B cell before transduction with BCL6 and an anti-apoptotic nucleic acid. Thus, culturing B cells in which somatic hyper mutation is induced by expression of AID allows the generation of immunoglobulin variants which, for example, have a higher or lower affinity for an antigen of interest, or that are more stable.

Although WO 2012/072814 describes that culturing of B cells wherein somatic hypermutation due to AID activity is induced may result in antibody variants which have a higher stability, it is also clear from WO 2012/072814 that the described selection methods wherein B cells are selected based on their binding capacity only do not specifically select for stable antibodies. Instead, WO 2012/072814 discloses that variants with a higher affinity for the antigen of interest are selected using such selection methods. Accordingly, WO 2012/072814 repeatedly refers to “high affinity B cells according to the invention”. Contrary, the present invention provides selection methods for specifically identifying B cells which have a higher stability.

A method according to the present invention, using B cells, thus provides the advantage that the stability of antibodies can easily be taken into account and improved already during the early stages of development of antibodies, for instance therapeutic antibodies. This reduces or obviates the need to improve stability of antibodies that have already been selected based on their binding and/or affinity characteristics by introducing mutations in the nucleic acid encoding the antibody and testing the resulting antibodies for their stability much later in the development process. Such recombinant methods to improve stability of antibodies specific for an antigen of interest currently used generally first require determination of the amino acid sequence of the antibody. Subsequently one or more mutations are introduced into the sequence of the nucleic acid encoding the antibody, at multiple possible locations in the nucleic acid sequence so that a large number of mutated antibodies can be produced. Then, the genes containing one or more mutations need to be expressed in a cell followed by production of antibodies in producer cells. Finally, the mutated antibodies are tested for their stability in order to determine whether antibody with an improved stability is obtained. Such a process for improving the stability of an antibody is elaborate and time-consuming. A method according to the present invention allows the selection of stable antibody in a straight-forward and less elaborate process without the need of molecular engineering in the same stage of development as selecting for binding avidity and/or affinity of the antibody. Using a method of the present invention antibodies are produced in ex vivo B cell cultures. Once B cells capable of producing antibodies specific for an antigen of interest have been obtained the B cells can be cultured during which differences in affinity and stability occur as a result of mutations introduced during such culturing. The B cell culture thus consists of a vast amount of B cells which are all specific for the antigen of interest but which vary in the affinity for the antigen and in the stability of the antigen. In this culture of antigen specific B cells, a small subgroup of B cells will have a particularly high stability as compared to the average stability of B cells in the B cell culture. Before the present invention, considering the small amount of B cells producing antibodies with the desired high stability, selection for stability of antibodies would have required testing of antibodies produced by a large number of B cells in order to identify antibodies with the desired high stability. As detailed above, the invention provides the insight that a correlation exists between a high binding avidity of B cells to an antigen of interest and a high stability of antibodies produced by these B cells. Thus, the subset of B cells capable of producing highly stable antibodies within the subset of B cells with a high binding avidity for a specific antigen is much larger than the subset of B cells capable of producing highly stable antibodies within the entire B cell culture. Hence, when selecting B cells which have a high binding avidity for an antigen, at the same time a pre-selection of B cells capable of producing highly stable antibodies is made. Antibodies obtained from only a limited number of B cells now need to be tested for stability. This is advantageous because the selection of high binding avidity B cells is relatively fast, easy and less expensive as compared to the testing of antibodies for their stability.

The methods of the present invention wherein production of antibodies by ex vivo B cell cultures are used allow the fast, easy and cost effective selection of antibodies having a specificity for an antigen of interest which in addition have a high stability. I.e. the present invention allows for the inclusion of stability as a parameter in the selection of antibodies at an early stage of development. Preferred methods for producing stable ex vivo B cell cultures from which stable antibodies are selected in accordance with the present invention are the methods as for instance described in WO 2007/067046, which is incorporated herein by reference. In a method as disclosed in WO 2007/067046, a collection of B cells obtained from a human individual is maintained in culture using BCL6 nucleic acid and an anti-apoptotic nucleic acid (or compounds increasing the expression of such nucleic acids) and subsequently cultured. This results in human B cells, which are capable of both proliferating and producing antibody for a prolonged period of time (up to >6 months). In a method of the present invention, these B cells are tested for their binding avidity for a specific antigen. One or more B cells selected for having a high binding avidity are preferably further expanded into a further B cell culture. During culturing, the stabilized B cells produce antibody, which is secreted into the culture medium. In a method of the present invention, these antibodies are tested for stability, and optionally for affinity for the antigen. For these test procedures, a minimum antibody concentration of approximately 100 ng/ml culture medium is typically used. The time required for obtaining this minimal concentration of antibodies after a high binding avidity B cell has been selected and expanded depends on the mammal from which the B cells was originally isolated. For stabilized human B cells, such antibody concentration is typically obtained after 15-20 days of culturing starting from a single B cell. Therefore, using human B cell cultures, antibody is harvested at least 15-20 days after starting a single B cell culture, typically around day 20. Llama B cells have a similar growth rate as human B cells, so that if a llama B cell culture is used, antibody is also typically harvested at least 15-20 days after starting a single B cell culture. With murine B cells, which have a longer doubling time, antibodies with a minimal concentration of 100 ng/ml are typically obtained after more than 20 days after starting a single B cell culture. When using rabbit B cells, an antibody concentration of at least 100 ng/ml is already obtained after 11-12 days after starting a single B cell culture. As the skilled person will appreciate, the desired antibody concentration may be obtained at an earlier time point if culturing is started from more than one B cell.

Preferably, in a method of the invention the stability of antibodies produced by the at least one B cell selected as having a binding avidity higher than the average binding avidity of B cells in the B cell culture from which the at least one B cell is obtained the stability of antibodies produced by a B cell culture after expansion of said at least one B cell selected as having a higher binding avidity is determined within four months from selecting said at least one B cell having a binding avidity higher than the average binding avidity of B cells in the B cell culture from which the at least one B cell is obtained. More preferably said stability is determined within three months from selecting said at least one B cell having a binding avidity higher than the average binding avidity of B cells in the B cell culture from which the at least one B cell is obtained, more preferably within two months. Most preferably, said stability is determined within one month from selecting said at least one B cell having a binding avidity higher than the average binding avidity of B cells in the B cell culture from which the at least one B cell is obtained, such as within between 12 and 30 days, more preferably within 12-25 days.

A B cell capable of producing antibody is defined as a B cell which is capable of producing and/or secreting antibody or a functional part thereof, and/or which cell is capable of developing into a cell which is capable of producing and/or secreting antibody or a functional part thereof. A functional part of an antibody is defined as a part which has at least one same property as said antibody in kind, not necessarily in amount. Said functional part is preferably capable of binding a same antigen as said antibody, albeit not necessarily to the same extent. A functional part of an antibody preferably comprises a single domain antibody, a single chain antibody, a FAB fragment, a nanobody, an unibody, a single chain variable fragment (scFv), or a $F(ab')_2$ fragment.

The binding avidity of a B cell according to the invention to an antigen of interest can be measured using any method known to a person skilled in the art. For instance, an antigen of interest is labelled with, for example, a fluorescent label. Detection of binding can subsequently be determined by various techniques, among which fluoresce microscopy and Fluorescence Activated Cell Sorting (FACS). FACS allows the separation of cells in a suspension for instance on the basis of size and/or the fluorescence of labeled antigen bound to the B cell receptor expressed on the cell surface of B cells.

Selecting at least one B cell with a high binding avidity for an antigen of interest from a of B cell culture, preferably from a monoclonal B cell line, can be performed using any method known to a person skilled in the art. Selection of at least one high-affinity B cell according to the invention is for instance performed by cell sorting for instance using FACS (see above), for instance during the same method in which binding avidity is measured, or by limited dilution. Limited dilution comprises the serial dilution of a suspension of cells, for instance B cells, until a single cell is present in a given volume. Subsequently, the binding avidity of each B cell (after expansion of single cells to a population) is tested to allow selection of a B cell producing antibodies with a high affinity for antigen.

Selecting at least one B cell with a binding avidity higher than the average binding avidity of the B cell culture from which the B cell is obtained, preferably involves determining the binding avidity of the B cell and determining the average binding avidity of B cells from the B cell culture.

Subsequently, the binding avidity of the at least one B cell is compared with the average binding avidity of B cells from the B cell culture and a B cell is selected that has a higher binding avidity than the average binding avidity of B cells from the B cell culture.

The term "stability" as used herein preferably refers to the chemical and/or physical stability of an antibody, for instance stability during production and/or storage of antibodies. Thus, stability as used herein preferably is chemical stability and/or physical stability, more preferably stability during production and/or storage of antibodies, more preferably thermal stability and/or resistance to aggregation. During production and storage antibodies in liquid formulations, such as pharmaceutical compositions, are susceptible to a variety of processes that influence the physical and/or chemical properties of the antibodies. Such processes include degradation, aggregation, oxidation, and fragmentation of the antibodies. Such processes are detrimental to the efficacy of antibodies because they result for instance in a decrease of the amount of functional antibodies in the formulation, and/or by reducing the antigen binding properties of the antibodies. Antibodies that are at least in part resistant to one or more of such processes are referred to as stable antibodies. Hence, determining the stability of antibodies produced by at least one B cell in a method of the invention preferably comprises determining the resistance of said antibodies to degradation, aggregation, oxidation and/or fragmentation. Further, antibodies produced by at least one B cell with a higher stability as compared to the average stability of antibodies produced by B cells of a B cell culture selected in accordance with a method of the invention thus preferably are antibodies that have a higher resistance to degradation, aggregation, oxidation and/or fragmentation as compared to the average resistance to degradation, aggregation, oxidation and/or fragmentation of antibodies produced by said B cells of a B cell culture. As used herein the term "a higher resistance to degradation, aggregation, oxidation and/or fragmentation" of an antibody as compared to the average resistance of antibodies means that the antibody exhibits less of a reduction or increase in molecular weight and/or alteration in structure within a given period of time under comparable conditions. The result of a higher resistance to degradation, aggregation, oxidation and/or fragmentation is that the loss of activity of such antibodies within a given period of time is less as compared to antibodies having an average resistance to degradation, aggregation, oxidation and/or fragmentation. Thus, poor stability of antibodies can result in subsets of non-functional antibodies, such as antibodies which have the propensity to form aggregates, antibody degradation products and chemically modified antibodies. In addition to losing their antigen-binding properties, such aggregates are potentially dangerous and/or immunogenic when administered to a patient. Poor stability may further for instance result in denaturation of antibodies which also results in a loss of function.

A "stable" antibody as used herein preferably refers to an antibody which essentially retains its physical and/or chemical stability and/or biological activity upon storage. Various methods are available in the art for measuring stability of proteins, including antibodies. For instance, stability can be measured at pre-determined temperatures for pre-determined periods of time. In the Examples two examples of such methods for determining the stability are detailed. The first method involves determining the thermal stability of antibodies, and is also referred to as dynamic scanning fluorescence or DSF. In this method, the unfolding of antibodies upon heating is determined. As the antibodies are heated, they unfold and a fluorescent dye is able to bind to the antibodies as they unfold. The dye becomes fluorescent when it binds to the unfolded antibodies and fluorescence is measured over time. For instance, the unfolding of the antibodies is measured over a temperature range of 30-95° C. Another method detailed in the Examples measures the tendency of antibodies to aggregate. This method involves separation of antibody monomers and aggregates of antibodies using gel chromatography. For instance, the tendency of antibodies to aggregate over time can be measured, whereby the amount of aggregated antibodies is measured after pre-determined periods of time of storage at a pre-determined temperature. For instance aggregation of antibodies is measured after 1, 2, 3, 4, 5, 6, 7, 8, 9 or 10 weeks or months of storage or before and after 0.5, 1, 1.5 and 2 years of storage. Storage is for instance at room temperature, at temperature of 4° C. to 7° C. or at temperature of −80° C. to −20° C. Stability of antibodies as used herein thus preferably refers to chemical stability and/or physical stability, more preferably stability during production and/or storage of antibodies. Stability of antibodies as used herein most preferably refers to thermal stability and/or resistance to aggregation. Preferably antibodies are selected that are stable for at least 1 year, more preferably for at least 18 months, and even more preferably for at least two years, at temperatures of between −80 and 80° C. More preferably antibodies are selected or B cells capable of producing antibodies are selected, which antibodies are stable for at least 1 year, more preferably for at least 18 months, and even more preferably for at least two years, at temperatures of between −80 and 80° C., preferably between −80 and 65° C., more preferably between 80 and 65° C., such as at room temperature, at a temperature of 4° C. to 7° C. or at a temperature of −80° C. to −20° C. Selected antibodies preferably have a shelf life of at least t least 1 year, more preferably for at least 18 months, and even more preferably for at least two years in a liquid formulations or in solid, e.g. freeze dried, formulations. Antibodies are considered stable for the indicated periods of time if they show no substantial aggregation, unfolding and/or denaturation during these periods of time With "no substantial aggregation, unfolding and/or denaturation" is meant that at most 20% of the antibodies, more preferably at most 10% of the antibodies, more preferably at most 5%, more preferably at most 2% of the antibodies aggregates, unfolds and/or denatures during the indicated period of time Most preferably at most 1% of the antibodies aggregates, unfolds and/or denatures during the indicated period of time.

Selecting at least one B cell capable of producing antibody with a stability higher than the average stability of antibodies produced by the B cell culture from which the B cell is obtained in accordance with the present invention preferably involves determining the stability of antibodies produced by the B cell and determining the average stability of antibodies produced by B cells from the B cell culture. Subsequently, the stability of antibody produced by the at least one B cell is compared with the average stability of antibodies produced by B cells from the B cell culture and a B cell is selected that is capable of producing antibody that has a higher stability than the average stability of antibodies produced by B cells from the B cell culture.

The average binding avidity of a B cell culture or of a population of B cells is herein defined as the average of the binding avidity of all individual B cells in said culture or population, respectively. A B cell selected from a B cell culture with a high binding avidity, preferably from a monoclonal B cell culture, is preferably selected from the upper 40% of the B cells of said B cell culture with respect to binding avidity, preferably from the upper 30% of the B cells of said culture more preferably from the upper 25% of the B cells of said B cell culture, more preferably from the upper 20% of the B cells of said B cell culture, more preferably from the upper 15% of the B cells of said B cell culture, more preferably from the upper 10% of the B cells of said B cell culture, more preferably from the upper 5% of the B cells of said B cell culture. Most preferably, one high binding avidity B cell is selected from the upper 1% of the B cells of a B cell culture with respect to binding avidity.

The average stability of antibodies produced by B cell of a B cell culture or of a population of B cells is herein defined as the average of the stability of antibodies produced by all individual B cells in said culture or population, respectively. A B cell selected from a B cell culture capable of producing antibodies with a high stability in accordance with the invention is preferably selected from the upper 40% of the B cells of said B cell culture with respect to the stability of the antibodies produced by said B cells, preferably from the upper 30% of the B cells of said culture more preferably from the upper 25% of the B cells of said B cell culture, more preferably from the upper 20% of the B cells of said B cell culture, more preferably from the upper 15% of the B cells of said B cell culture, more preferably from the upper 10% of the B cells of said B cell culture, more preferably from the upper 5% of the B cells of said B cell culture with respect to the stability of the antibodies produced by said B cells. Most preferably, a B cell capable of producing stable antibodies is selected from the upper 1% of the B cells of a B cell culture with respect to the stability of the antibodies produced by said B cells.

Whether or not an antibody produced by at least one B cell selected in accordance with the invention or produced in accordance with the invention has a higher stability as compared to the average stability of antibodies produced by B cells in the first (ex vivo) B cell culture is for instance determined using one or more of the assays described herein for determining stability of antibodies, or with alternative methods for determining stability of antibodies known in the art. If a difference in stability is observed in one or more of these assay's and the antibody selected in accordance with the invention or produced by an antibody selected in accordance with the invention shows a higher stability than antibodies produced by B cells in said first (ex vivo) B cell culture, it is concluded that the antibody selected in accordance with the invention or produced by an antibody selected in accordance with the invention has a higher stability as compared to the average stability of antibodies produced by B cells of said first (ex vivo) B cell culture.

The average stability of antibody produced by a B cell culture, preferably by a monoclonal B cell line, cultured from at least one B cell selected or produced in accordance with the invention is preferably at least 1.1 times the average stability of antibodies produced by B cells in the first (ex vivo) B cell culture from which the B cell capable of producing highly stable antibodies was selected, more preferably at least 1.2, 1.3, 1.4, 1.5, 1.6, 1.7, 1.8, 1.9, 2.0, 2.1, 2.2, 2.3, 2.4, 2.5, 3.0, 3.5, 4.0, 5.0, 10.0, 20, 50, 100 times, or more, than the average stability of antibodies produced by B cell in said first (ex vivo) B cell culture. Such factor of is for instance established using one or more of the assays described herein for determining stability of antibodies. For instance, in the assay described herein in which aggregation of antibody is measured, it is possible to calculate the percentage of antibodies in a sample that has aggregated. An antibody selected in accordance with the invention or produced by an antibody selected in accordance with the invention is for instance said to have a 1.2 times higher stability if the percentage of aggregated antibody in a sample is 1.2. times lower than the percentage of aggregated antibody produced by B cell in said first (ex vivo) B cell culture.

A method of the invention preferably further comprises determining the affinity for the antigen of interest of antibodies produced by a B cell selected for having a binding avidity that is higher than the average binding avidity of the (ex vivo) B cell culture from which the B cell is selected. Said affinity is preferably compared with the average affinity of antibodies produced by B cells from said B cell culture. The average affinity for an antigen of interest of an antibody produced by a B cell culture or by a population of B cells is herein defined as the average of the affinities for said antigen of interest of the antibodies produced by all individual B cells in said culture or population, respectively. A method of the invention thus preferably further comprises determining the affinity for the antigen of interest of antibodies produced by said at least one B cell selected for as having a high binding avidity or produced by the B cell culture from which said at least one B cell is selected; and selecting at least one B cell capable of producing antibodies with a higher affinity for the antigen as compared to the average affinity of antibodies produced by B cells of the B cell culture or by the ex vivo B cell culture from which said at least one B cell is selected.

In another preferred embodiment, however, a B cell is selected that is capable of producing antibodies which have an affinity for the antigen of interest that is similar to, or less than, the average affinity for said antigen of interest of antibodies produced by the B cell culture or by the ex vivo B cell culture from which said at least one B cell is selected. Such lower or average affinity is often sufficient in order to have sufficient functionality of the antibodies, such as their therapeutic activity. A high stability of the antibodies on the other hand is an absolute requirement for commercial production and (therapeutic) use of antibodies specific for an antigen of interest. I.e. it is more preferred to select an antibody with a method in accordance with the invention that has a particularly high stability but an average affinity or an affinity that is slightly less than average than to select a high affinity antibody that is unstable or has a relatively low stability. Now that the present invention establishes a correlation between the binding avidity of a B cell for an antigen of interest and the stability of antibodies produced by the B cell, it has become possible to select such highly stable antibody with average affinity for the antigen over an unstable antibody with a high affinity already at an early stage in antibody screening and development processes.

Provided is a method for producing a B cell capable of producing antibody for an antigen of interest comprising:

a) selecting at least one B cell capable of producing antibody specific for said antigen of interest or at least one B cell capable of developing into a B cell capable of producing antibody specific for said antigen of interest;

b) inducing, enhancing and/or maintaining expression of BCL6 and inducing, enhancing and/or maintaining expression of an anti-apoptotic nucleic acid in said at least one B cell;

c) allowing expansion of said at least one B cell into a first B cell culture;

d) selecting at least one B cell from said first B cell culture with a binding avidity for said antigen of interest that is higher than the average binding avidity for said antigen of interest of B cells in said first B cell culture;

e) preferably allowing expansion of said at least one B cell selected in step d) into a second B cell culture;

f) determining the stability, and affinity for said antigen of interest, of antibodies produced by said at least one B cell selected in step d) or by said second B cell culture; and g) selecting at least one B cell capable of producing antibodies with a higher stability as compared to the average stability of antibodies produced by B cells of said first B cell culture and with an affinity for said antigen of interest that is similar to, or less than, the average affinity for said antigen of interest of or of antibodies produced by said first B cell culture.

Further provided is a method for selecting from an ex vivo B cell culture at least one B cell capable of producing antibodies with a higher stability as compared to the average stability of antibodies produced by said ex vivo B cell culture, the method comprising:

a) providing an ex vivo B cell culture capable of producing antibody specific for an antigen of interest;

b) selecting at least one B cell from said ex vivo B cell culture with a binding avidity for said antigen of interest that is higher than the average binding avidity of B cells of said ex vivo B cell culture for said antigen of interest;

c) determining the stability, and affinity for said antigen, of interest of antibodies produced by said at least one B cell selected in step b); and d) selecting at least one B cell capable of producing antibodies with a higher stability as compared to the average stability of antibodies produced by B cells of said ex vivo B cell culture and with an affinity for said antigen of interest that is similar to, or less than, the average affinity for said antigen of interest of or of antibodies produced by said ex vivo B cell culture.

The affinity of an antibody can be determined using any method known to a person skilled in the art. The affinity of an antibody is for instance determined using Enzyme-linked immunosorbent assay (ELISA), Surface Plasmon Resonance (such as Biacore) or Octet (ForteBio). Surface Plasmon Resonance (SPR) and Octet are techniques to measure biomolecular interactions in real-time in a label free environment. For SPR, one of the interactants, for instance an antibody, is immobilized to the sensor surface, the other, for instance antigen, is free in solution and passed over the surface. Association and dissociation is measured in arbitrary units and preferably displayed in a sensorgram. Any change in the number of molecules bound to the biosensor tip causes a shift in the interference pattern that can be measured in real-time Using Octet the interference pattern of white light reflected from two surfaces, a layer of immobilized protein on the biosensor tip, and an internal reference layer is analyzed. The binding between a ligand immobilized on the biosensor tip surface, for instance an antibody, and a protein in solution, for instance an antigen of interest, produces an increase in optical thickness at the biosensor tip, which results in a wavelength shift which is a direct measure of the change in thickness of the biological layer. ELISA comprises immobilizing a protein, for instance the antigen of interest, on the surface of the solid support, for example a 96-well plate, and applying a sample to be detected or quantified on the solid support. Alternatively, a capture antibody is fixated on the surface of a solid support after which a sample containing the protein to be detected or quantified is applied to the immobilized capture antibody allowing the protein of interest to bind. Non-binding proteins are than washed away. Subsequently a specific antibody conjugated to a label or an enzyme (or a primary antibody followed by a secondary antibody conjugated to a label or an enzyme) is added to the solid support. Preferably the affinity constant ($K_D$) of an antibody produced by a B cell according to the invention is determined.

Selecting at least one B cell capable of producing antibody with an affinity for a specific antigen higher than, similar to, or lower than the average affinity of antibodies produced by the B cell culture from which the B cell is obtained, preferably involves determining the affinity of antibody produced by the B cell for the antigen and determining the average affinity of antibodies produced by B cells from the B cell culture for the antigen. Subsequently, the affinity for the antigen of antibody produced by the at least one B cell is compared with the average affinity for the antigen of antibodies produced by B cells from the B cell culture and a B cell is selected that is capable of producing antibodies that have a higher, similar, or lower affinity than the average affinity of antibodies produced by B cells from the B cell culture.

A B cell culture or an ex vivo B cell culture in accordance with the present invention preferably is a monoclonal B cell culture. An example of a B cell culture or an ex vivo B cell culture in accordance with the present invention is a cell line of B cells, preferably monoclonal B cells. Hence, a B cell culture or an ex vivo B cell culture in accordance with the present invention is most preferably a monoclonal B cell line. Allowing expansion of a B cell selected on its binding or stability properties into a B cell culture is for instance accomplished by allowing expansion of said B cell until a population of B cells is obtained.

Non-limiting examples of a B cell used or selected in a method according to the invention include B cells derived from a human individual, a rodent, a rabbit, a llama, a pig, a cow, a goat, a horse, an ape, a chimpanzee, a macaque and a gorilla. Preferably, said B cell is a human cell, a murine cell, a rabbit cell, an ape cell, a chimpanzee cell, a macaque cell and/or a llama cell. Most preferably, said B cell is a human B cell or a rabbit B cell. Preferably, a B cell capable of producing antibody specific for an antigen of interest that is selected in accordance with a method of the invention in which expression of BCL6 and an anti-apoptotic nucleic acid is induced, enhanced and/or maintained is a memory B cell, for instance a human memory B cell or a rabbit memory B cell. Particularly preferred is a peripheral blood memory B cell. Peripheral blood memory B cells are easily obtained, without much discomfort for the individual from which they are obtained, and have been demonstrated to be very suitable for use in a method according to the present invention.

Within a, preferably monoclonal, B cell culture of B cells capable of producing antibody specific for an antigen of interest, it is possible to select at least one, optionally more than one, such as for instance 2, 3, 4, 5, 6, 7, 8, 9, 10, 20, 25, 50, 100, $10^3$, $10^4$, $10^5$ or $10^6$ B cells with a binding avidity for said antigen of interest that is higher than the average binding avidity of said B cell culture for said antigen of interest. As described in WO 2012/072814, a subset of B cells in a given B cells culture produce antibodies specific for the antigen of interest shows a higher binding to said antigen, which is correlated to the fact that antibodies produced by said subset of B cells have a higher affinity for the antigen than the average affinity of antibodies produced by said B cell culture. The present invention provides the insight that another subset of B cells that have a higher binding avidity for the antigen produce antibodies which have a higher stability than the average stability of antibodies produced by said B cell culture. As further described in WO 2012/072814 the B cell cultures obtained after culturing antibody producing B cells which produce high affinity antibodies contains B cells of which the antibodies maintained the ability to bind antigen with a higher affinity than the average B cell in the original B cell culture. The same applies to the subset of B cell producing antibodies with high stability: B cell cultures obtained after culturing such high stability antibody producing B cells contains B cells that produce antibodies with a higher stability than the average B cell in the original B cell culture. Single B cells can thus be isolated from a given B cell culture on the basis of their higher binding avidity by methods known in the art and be expanded to a new B cell culture of which the average stability of produced antibodies is higher than the average stability of B cells in said given B cell culture.

In a method according to the invention preferably a single B cell is selected that is specific for an antigen of interest, for instance from a polyclonal B cell population obtained from an individual. The single B cell is subsequently preferably expanded into a monoclonal B cell culture. This is for instance achieved using a method as described in WO 2007/067046, which is discussed herein before. Hence, a monoclonal B cell line specific for an antigen of interest is obtained. In principle, all B cells in the monoclonal B cell line produce essentially the same antibodies specific for said antigen, although small differences in the stability of antibodies may be present between B cells of said monoclonal B cell line, i.e. some B cells in the monoclonal culture produce antibodies with a stability which is slightly higher than the average stability and some B cells in the monoclonal culture produce antibodies with a slightly lower stability. The B cell culture becomes slightly heterogeneous again. In accordance with the invention at least one B cell with a higher binding avidity than the average binding avidity is selected from the monoclonal B cell line. Of all the B cells with a higher binding avidity than the average binding avidity, a subset produces antibodies with a higher stability than the average stability of antibodies produced by B cells in the B cell culture. In accordance with the invention subsequently at least one of such B cells producing antibodies with a higher stability than the average stability is selected. A selected B cell is or selected B cells are subsequently preferably cultured into a second, preferably monoclonal, B cell culture. The present invention provides the insight that this second, preferably monoclonal, B cell culture produces antibodies with an average stability that is higher than the average stability of the original (monoclonal) B cell culture. As described above, it was found that the high stability of antibodies produced by a selected B cell is maintained after culturing, even if culturing takes place during a prolonged period of time. Thus, antibodies produced by the second (monoclonal) B cell culture obtained in accordance with the invention have a higher average stability than antibodies produced by the first (monoclonal) B cell culture.

As detailed herein before, preferably one B cell is selected that is capable of producing antibodies with a stability that is higher than the average stability of antibodies produced by the B cell culture from which the B cell is selected. In another embodiment, more than one of such B cells capable of producing antibodies with such higher stability is selected, for instance 2, 3, 4, 5, 10, 15, 25, 50, 100, $10^3$, $10^4$, $10^5$, $10^6$ B cells. The B cells are for instance selected from a polyclonal B cell culture or from a biological sample. The B cells are subsequently expended into a B cell culture, for instance using a method as described in WO 2007/067046. The obtained B cell culture is in this case thus a (second) polyclonal B cell culture. Thereafter, a monoclonal B cell culture is preferably produced. This is for instance done by selecting a single B cell from said (second) polyclonal B cell culture using Fluorescence Activated Cell Sorting (FACS) or limiting dilution, as described herein, and expanding said selected single B cell to a monoclonal B cell culture. Then, preferably at least one B cell with a higher binding avidity than the average binding avidity of the monoclonal B cell culture and which is capable of producing antibodies with a higher stability than the average stability of antibodies produced by the monoclonal B cell culture is selected. The selected B cell is preferably subsequently cultured into a second monoclonal B cell culture, after which antibodies produced by said second monoclonal B cell line can be obtained. Preferably, the amino acid sequence of at least part of the heavy chain and light chain of the antibodies are determined and compared with the amino acid sequence of (the relevant part of) the heavy and light chain of the antibodies produced by the (ex vivo) B cell culture from which a B cell was originally selected. This way the mutation(s) in the amino acid sequence that promotes the increased stability of the antibody can be identified. A preferred method further comprises expressing a nucleic acid molecule encoding the heavy chain and/or light chain of the antibody with increased stability in a second cell. Said second cell is preferably a so-called producer cell, such as for instance a cell of a Chinese hamster ovary (CHO), NSO (a mouse myeloma) or 293(T) cell line, which are preferably adapted to commercial antibody production. Proliferation of such producer cells results in a producer cell line capable of producing stable antibodies according to the invention.

In one embodiment of the invention, after the step of selecting at least one B cell producing high stability antibodies from said already monoclonal B cell culture, said at least one B cell is allowed to expand into a B cell culture, preferably a monoclonal B cell line, again, after which another step of selecting at least one B cell producing high stability antibodies from said new B cell culture, preferably from said new monoclonal B cell line, is performed. By repeating the steps of allowing expansion of a selected B cell into a B cell culture and selecting at least one B cell on the basis of its binding avidity and/or on the basis of the stability of antibodies produced by it, it is possible to generate high affinity antibody producing B cells. Preferably, by repeating the steps of expansion and selection as described above, it is possible to increase with each selection cycle the stability of antibody produced by the resulting B cell culture.

In a preferred embodiment in a method for selecting from an ex vivo B cell culture at least one B cell capable of producing antibodies with a higher stability than the average stability of antibodies produced by said ex vivo B cell culture according to the invention step a) comprises selecting at least one B cell capable of producing antibody specific for said antigen of interest or selecting at least one B cell capable of developing into a B cell capable of producing antibody specific for said antigen of interest and allowing expansion of said at least one B cell into said ex vivo B cell culture. Preferably, allowing expansion of said at least one B cell into said ex vivo B cell culture and selecting at least one B cell from said ex vivo B cell culture capable of producing antibody with a binding avidity for said antigen of interest that is higher than the average binding avidity of B cell receptors or antibodies produced by said ex vivo B cell culture for said antigen of interest in step b) are repeated at least once. Said steps may be repeated twice, three times, four times, five times or even more times.

Further provided is a method for selecting from an ex vivo B cell culture at least on B cell capable of producing antibodies with a higher stability as compared to the average stability of antibodies produced by said ex vivo B cell culture in accordance with the invention is thus provided wherein step a) comprises selecting at least one B cell capable of producing antibody specific for said antigen of interest or selecting at least one B cell capable of developing into a B cell capable of producing antibody specific for said antigen of interest and allowing expansion of said at least one B cell into said ex vivo B cell culture, and wherein allowing expansion of said at least one B cell into said ex vivo B cell culture and selecting at least one B cell from said ex vivo B cell culture capable of producing antibody with a binding avidity for said antigen of interest that is higher than the average binding avidity of B cell receptors or antibodies produced by said ex vivo B cell culture for said antigen of interest in step b) are repeated at least once. Said steps are for instance repeated once, but preferably twice, three times, four times, five times or even more times.

A method of the invention preferably comprises inducing, enhancing and/or maintaining expression of BCL6 in a B cell and/or a (ex vivo) B cell culture. BCL6 encodes a transcriptional repressor which is required for normal B cell and T cell development and maturation and which is required for the formation of germinal centers. BCL6 is highly expressed in germinal center B cells whereas it is hardly expressed in plasma cells. BCL6 inhibits differentiation of activated B cells into plasma cells. In a method according to the invention, BCL6 expression product remains present in the B cells of an ex vivo culture. The presence of BCL6 together with the presence of an anti-apoptotic nucleic acid, prolongs the replicative life span of the B cells. Expression of BCL6 is preferably induced, enhanced or maintained by administering a BCL6 expression-promoting compound to the B cell(s) used for culturing, or by culturing B cells in the presence of such compound.

Various compounds capable of directly or indirectly enhancing expression of BCL6 are known in the art. Such compound for instance comprises a Signal Transducer of Activation and Transcription 5 (STAT5) protein, or a functional part or a functional derivative thereof, and/or a nucleic acid sequence coding therefore. STAT5 is a signal transducer capable of enhancing BCL6 expression. There are two known forms of STAT5, STAT5a and STAT5b, which are encoded by two different, tandemly linked genes. Administration and/or activation of STAT5 results in enhanced levels of BCL6. Hence, STAT5, or a functional part or a functional derivative thereof is capable of directly increasing expression of BCL6. Provided is therefore a method according to the invention comprising providing the B cell(s) with STAT5, or with a functional part or a functional derivative thereof, or providing the B cell(s) with a nucleic acid molecule encoding STAT5, or a functional part or a functional derivative thereof, or culturing said B cell in the presence of STAT5, or a functional part or a functional derivative thereof.

The presence of STAT5 directly increases the amount of BCL6. It is also possible to indirectly increase expression of BCL6. This is for instance done by regulating the amount of a certain compound, which in turn is capable of directly or indirectly activating STAT5 and/or increasing expression of STAT5. Hence, in one embodiment the expression and/or activity of endogenous and/or exogenous STAT5 is increased. It is for instance possible to indirectly enhance expression of BCL6 by culturing a B cell in the presence of interleukin (IL) 2 and/or IL4 which are capable of activating STAT5, which in turn increases expression of BCL6.

It is, however, preferred to provide a B cell with a nucleic acid molecule encoding BCL6, or a functional part or a functional derivative thereof. This way, it is possible to directly regulate the concentration of BCL6 in said B cell. Also provided is therefore a method according to the invention comprising providing said B cell with a nucleic acid molecule encoding BCL6, or a functional part or a functional derivative thereof. In one embodiment, said nucleic acid molecule is constitutively active, meaning that BCL6, or a functional part or a functional derivative thereof, is continuously expressed, independent of the presence of a regulator. In another embodiment, said nucleic acid molecule is inducible, meaning that the expression thereof is regulated by at least one inducer and/or repressor. This way, expression of said nucleic acid molecule is regulated at will. For instance, Tet-On and Tet-Off expression systems (for example Tet-On® and Tet-Off® Advanced Inducible Gene Expression Systems, Clontech) can be used for inducible expression of a nucleic acid sequence of interest. In these systems expression of the transcriptional activator (tTA) is regulated by the presence (Tet-On) or absence (Tet-Off) of tetracycline (TC) or a derivative like doxycycline (dox). In principle, tTA is composed of the *Escherichia coli* Tet repressor protein (TetR) and the *Herpes simplex* virus transactivating domain VP16. tTA regulates transcription of a nucleic acid sequence of interest under the control of a tetracycline-responsive element (TRE) comprising the Tet operator (TetO) DNA sequence and a promoter sequence, for instance the human cytomegalovirus (hCMV) promoter. A nucleic acid sequence encoding, for instance, Bcl6, or a functional part or a functional derivative thereof, can be placed downstream of this promoter.

In the Tet-off system, tTA binds to TRE in the absence of TC or dox and transcription of a nucleic acid sequence of interest is activated, whereas in the presence of TC or dox tTA cannot bind TRE and expression of a nucleic acid sequence of interest is inhibited. In contrast, the Tet-on system uses a reverse tTA (rtTA) that can only bind the TRE in the presence of dox. Transcription of a nucleic acid sequence of interest is inhibited in the absence of dox and activated in the presence of dox. Alternatively, inducible expression is executed using a hormone inducible gene expression system such as for instance an ecdysone inducible gene expression system (for example RheoSwitch®, New England Biolabs) (Christopherson, K. S. et al. PNAS 89, 6314-8 (1992)). Ecdysone is an insect steroid hormone from for example *Drosophila melanogaster*. In cells transfected with the ecdysone receptor, a heterodimer consisting of the ecdysone receptor (Ecr) and retinoid X receptor (RXR) is formed in the presence of an ecdyson agonist selected from ecdysone, one of its analogues such as muristerone A and ponasterone A, and a non-steroid ecdysone agonist. In the presence of an agonist, Ecr and RXR interact and bind to an ecdysone response element that is present on an expression cassette. Exaperssion of a nucleic acid sequence of interest that is placed in an expression cassette downstream of the ecdysone response element is thus induced by exposing a B cell to an ecdyson agonist.

As another example of the invention inducible expression is executed using an arabinose-inducible gene expression system (for example pBAD/gIII kit, Invitrogen) (Guzman, L. M. et al. Bacteriol 177, 4121-4130 (1995)). Arabinose is a monosaccharide containing five carbon atoms. In cells transfected with the arabinose-inducible promoter PBAD expression of a nucleic acid sequence of interest placed downstream of PBAD can then be induced in the presence of arabinose.

It is also possible to use (a nucleic acid molecule encoding) a BCL6 protein, or a functional part or functional derivative thereof, wherein the activity of said BCL6, or functional part or functional derivative is regulated by at least one inducer and/or repressor. A non-limiting example is a fusion protein wherein a regulatory element is fused to a sequence encoding at least part of BCL6. For instance, an estrogen receptor (ER) is fused to BCL6, resulting in fusion protein ER-BCL6. This fusion protein is inactive because it forms a complex with heat shock proteins in the cytosol. Upon administration of the exogenous inducer 4 hydroxy-tamoxifen (4HT), the fusion protein ER-BCL6 dissociates from the heat shock proteins, so that the BCL6 part of the fusion protein becomes active.

A method of the invention preferably comprises inducing, enhancing and/or maintaining expression of an anti-apoptotic nucleic acid in a B cell and/or a (ex vivo) B cell culture. As used herein, the term "anti-apoptotic nucleic acid molecule" refers to a nucleic acid molecule, which is capable of delaying and/or preventing apoptosis in a B cell. Preferably, said anti-apoptotic nucleic acid molecule is capable of delaying and/or preventing apoptosis in a plasmablast-like B cell, which is capable of both proliferating and producing antibody. Preferably, an anti-apoptotic nucleic acid molecule is used which comprises an exogenous nucleic acid molecule. This means that either a nucleic acid sequence is used which is not naturally expressed in B cells, or that an additional copy of a naturally occurring nucleic acid sequence is used, so that expression in the resulting B cells is enhanced as compared to natural B cells. Various anti-apoptotic nucleic acid molecules are known in the art, so that various embodiments are available. Preferably, an anti-apoptotic nucleic acid molecule is used which is an anti-apoptotic member of the Bcl-2 family because anti-apoptotic Bcl-2 proteins are good apoptosis inhibiters in B cells. Many processes that are controlled by the Bcl-2 family (which family includes both pro- and anti-apoptotic proteins) relate to the mitochondrial pathway of apoptosis. The use of anti-apoptotic Bcl-2 family members Bcl-2, Bcl-xL, Bcl-w, Bcl-2-related protein A1 (also named Bcl2-A1 or A1), Bcl-2 like 10 (Bcl2L10) and Mcl-1, or a functional part or functional derivative thereof, is preferred because Bcl-2, Bcl-xL, Bcl-w, A1, Bcl2L10 and Mcl-1 are generally integrated with the outer mitochondrial membrane. They directly bind and inhibit the pro-apoptotic proteins that belong to the Bcl-2 family to protect mitochondrial membrane integrity.

Preferred is therefore a method according to the invention, wherein said anti-apoptotic nucleic acid molecule comprises an anti-apoptotic gene of the Bcl2 family, preferably Bcl-xL or Mcl-1 or Bcl-2 or A1 or Bcl-w or Bcl2L10, or a functional part or a functional derivative thereof.

Preferably, expression of Bcl-xL or Mcl-1 or Bcl-2 or A1 or Bcl-w or Bcl2L10, is induced, enhanced or maintained by administering at least one compound, capable of promoting expression of any of these anti-apoptotic genes, to B cell(s), or by culturing B cells in the presence of such compound(s). Further provided is therefore a method according to the invention, comprising:

providing said B cell with a compound capable of directly or indirectly enhancing expression of Bcl-xL and/or Mcl-1 and/or Bcl-2 and/or A1 and/or Bcl-w and/or Bcl2L10; and/or culturing said B cell in the presence of a compound capable of directly or indirectly enhancing expression of Bcl-xL and/or Mcl-1 and/or Bcl-2 and/or A1 and/or Bcl-w and/or Bcl2L10.

More preferably, however, a B cell is provided with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and functional parts and functional derivatives thereof. This way, it is possible to directly enhance the amount of expression product in said B cell. Also provided is therefore a method according to the invention, comprising providing said B cell with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and functional parts and functional derivatives thereof. In one embodiment, said nucleic acid molecule is constitutively active, meaning that said nucleic acid molecule is continuously expressed. In another embodiment, said nucleic acid molecule is inducible, meaning that the expression thereof is regulated by at least one inducer and/or repressor. Non-limiting examples of inducible nucleic acid expression systems known in the art are described herein before.

In a particularly preferred embodiment said anti-apoptotic nucleic acid molecule encodes Bcl-xL or Mcl-1, or a functional part or a functional derivative thereof, most preferably Bcl-xL or Mcl-1. According to the present invention, a combination of BCL6 and Bcl-xL is particularly well capable of increasing the replicative life span of B cells, thereby forming long term cultures of the resulting plasmablast-like B cells. The same holds true for a combination of BCL6 and Mcl-1. Most preferably, said anti-apoptotic nucleic acid encodes Bcl-xL or a functional part or a functional derivative thereof, and most preferably encodes Bcl-xL.

A functional part of BCL6, Bcl-xL, Mcl-1, Bcl-2, A1, Bcl-w or Bcl2L10 is a proteinaceous molecule that has the same capability—in kind, not necessarily in amount—of increasing the replicative life span of a B cell as compared to natural BCL6, Bcl-xL, Mcl-1, Bcl-2, A1, Bcl-w or Bcl2L10, respectively. Such functional part is for instance devoid of amino acids that are not, or only very little, involved in said capability.

For instance, functional parts of Bcl-xL, Mcl-1, Bcl-2, A1, Bcl-w and Bcl2L10 are defined herein as fragments of Bcl-xL, Mcl-1, Bcl-2, A1, Bcl-w and Bcl2L10, respectively, which have retained the same kind of anti-apoptotic characteristics as full length Bcl-xL, Mcl-1, Bcl-2, A1, Bcl-w and Bcl2L10, respectively (in kind, but not necessarily in amount). Functional parts of Bcl-xL, Mcl-1, Bcl-2, A1, Bcl-w or Bcl2L10 are typically shorter fragments of Bcl-xL, Mcl-1, Bcl-2, A1, Bcl-w or Bcl2L10, respectively, which are capable of delaying and/or preventing apoptosis in a B cell. Such functional parts are for instance devoid of sequences which do not significantly contribute to the anti-apoptotic activity of Bcl-xL, Mcl-1, Bcl-2, A1, Bcl-w and Bcl2L10. A functional part of BCL6 is typically a shorter fragment of BCL6 which is capable of increasing the replicative life span of a B cell.

A functional derivative of BCL6, Bcl-xL, Mcl-1, Bcl-2, A1, Bcl-w or Bcl2L10 is defined as a BCL6, Bcl-xL, Mcl-1, Bcl-2, A1, Bcl-w or Bcl2L10 protein, respectively which has been altered but has maintained its capability (in kind, not necessarily in amount) of increasing the replicative life span of a B cell. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Furthermore, a method according to the invention is provided, further comprising providing said B cell with IL21 and CD40L. Preferably, said IL21 is murine or human IL21, most preferably murine IL21. Said CD40L is also preferably murine or human CD40L, most preferably human CD40L.

Besides increasing BCL6 expression and the expression of an anti-apoptotic nucleic acid molecule, it is also advantageous to induce, enhance and/or maintain expression of Blimp-1 in a B cell. This enhances antibody production of said B cell. One aspect thus provides a method according to the invention, wherein the method further comprises inducing, enhancing and/or maintaining expression of Blimp-1 in said B cell. Blimp-1 expression is preferably induced or enhanced.

The extent of expression of Blimp-1 in a B cell can be regulated in a variety of ways. For instance a B cell is provided with a compound, which is capable of directly or indirectly increasing expression of Blimp-1 Additionally, or alternatively, a B cell is cultured in the presence of a compound capable of directly or indirectly increasing expression of Blimp-1. Further provided is a method according to the invention, further comprising:

providing said B cell with a compound capable of directly or indirectly increasing expression of Blimp-1; and/or culturing said B cell in the presence of a compound capable of directly or indirectly increasing expression of Blimp-1.

Said compound capable of increasing expression of Blimp-1 preferably comprises IL21. Hence, provided is a method wherein B cells are cultured in the presence of IL21, at least during part of the culture time.

Another preferred compound capable of increasing Blimp-1 expression comprises a Signal Transducer of Activation and Transcription 3 (STAT3) protein or a functional part or a functional derivative thereof, and/or a nucleic acid molecule coding therefore. STAT3 is a signal transducer, which is involved in B cell development and differentiation. STAT3 is capable of upregulating Blimp-1 expression. In another preferred method, a B cell is thus provided with a nucleic acid molecule encoding STAT3 or a functional part or a functional derivative thereof, preferably wherein the expression of said nucleic acid molecule is regulated by an exogenous inducer of repressor, so that the extent of STAT3 expression is regulated at will. For instance, one of the earlier mentioned inducible expression systems is used. For instance, a fusion product comprising STAT3, or a functional part or a functional derivative, and ER is used and a B cell is provided with a nucleic acid molecule encoding an estrogen receptor (ER) and STAT3 as a fusion protein ER-STAT3. This fusion protein is inactive because it forms a complex with heat shock proteins in the cytosol. This way, STAT3 is unable to reach the nucleus and Blimp-1 expression is not enhanced. Upon administration of the exogenous inducer 4 hydroxy-tamoxifen (4HT), the fusion protein ER-STAT3 dissociates from the heat shock proteins, so that STAT3 is capable of entering the nucleus and activating Blimp-1 expression.

As used herein, a functional part of STAT3 is defined as a fragment of STAT3 that has the same capability—in kind, not necessarily in amount—of increasing expression of Blimp-1 as compared to natural STAT3. Such functional part is for instance devoid of amino acids that are not, or only very little, involved in said capability.

A functional derivative of STAT3 is defined as a STAT3 protein, which has been altered but has maintained its capability (in kind, not necessarily in amount) of increasing expression of Blimp-1. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Since STAT3 is capable of increasing expression of Blimp-1 it is also possible to indirectly increase expression of Blimp-1 by administering a compound capable of increasing the activity and/or expression of STAT3. In one embodiment, a B cell is therefore provided with a compound that is capable of enhancing the activity of STAT3, so that expression of Blimp-1 is indirectly enhanced.

STAT3 is activated in a variety of ways. Preferably, STAT3 is activated by providing a B cell with a cytokine. Cytokines, being naturally involved in B cell differentiation, are very effective in regulating STAT proteins. Very effective activators of STAT3 are IL21 and IL6, but also IL2, IL7, IL10, IL15 and IL27 are known to activate STAT3. Moreover, Toll-like receptors (TLRs), which are involved in innate immunity, are also capable of activating STAT3. In a preferred method of the invention a B cell is therefore cultured in the presence of IL21, IL2, IL6, IL7, IL10, IL15 and/or IL27. Most preferably IL21 is used, since IL21 is particularly suitable for enhancing antibody production of B cell cultures according to the present invention. IL21 is capable of upregulating Blimp-1 expression, even when Blimp-1 expression is counteracted by BCL6.

Additionally, or alternatively a mutated Janus kinase (JAK) is used in order to activate STAT3. Naturally, a JAK is capable of phosphorylating STAT3 after it has itself been activated by at least one cytokine. A mutated Janus kinase capable of activating STAT3 independently of the presence of cytokines, is particularly suitable in a method according to the present invention.

In yet another embodiment, expression of Blimp-1 is increased by providing a B cell with a suppressor of cytokine signalling (SOCS) protein and/or by activating a SOCS protein within said cell. Alternatively, or additionally, at least one of the E-proteins E47, E12, E2-2 and HEB is used in order to increase expression of Blimp-1. E47 is a transcription factor that belongs to a family of helix-loop-helix proteins, named E-proteins. There are four E-proteins, E12, E47, E2-2 and HEB, which are involved in lymphocyte development. E12 and E47 are encoded by one gene, named E2A, which is spliced differently. E proteins have been described as tumor suppressors. One of the specific targets of E47 are the Socs1 and Socs3 genes.

The invention further provides isolated or recombinant B cells obtainable with a method according to the presence invention. Such isolated or recombinant B cells preferably comprise an exogenous anti-apoptotic nucleic acid sequence and an exogenous nucleic acid sequence encoding BCL6 or STAT5, or a functional part or a functional derivative thereof. Further provided is therefore an isolated or recombinant B cell, comprising an exogenous nucleic acid sequence encoding BCL6 or STAT5, or a functional part or a functional derivative thereof, and an exogenous anti-apoptotic nucleic acid sequence. As explained before, said exogenous nucleic acid molecule either contains a nucleic acid sequence that does not naturally occur in B cells, or an additional copy of a natural B cell nucleic acid sequence. Bcl-xL, Mcl-1, Bcl-2, A1, Bcl-w and Bcl2L10, are preferred anti-apoptotic nucleic acid molecules. Preferred is therefore an isolated or recombinant B cell, which comprises an exogenous nucleic acid sequence encoding BCL6 or STAT5, or a functional part or a functional derivative thereof, and an exogenous nucleic acid sequence encoding Bcl-xL or Mcl-1 or Bcl-2 or A1 or Bcl-w or Bcl2L10, or a functional part or a functional derivative thereof. Said nucleic acid sequence encoding BCL6 or STAT5, or a functional part or a functional derivative thereof, and said exogenous anti-apoptotic nucleic acid sequence may be present on one nucleic acid molecule. Alternatively, these sequences are present on at least two different nucleic acid molecules.

Provided is a method for producing a B cell capable of producing antibody for an antigen of interest comprising:

a) selecting at least one B cell capable of producing antibody specific for said antigen of interest or at least one B cell capable of developing into a B cell capable of producing antibody specific for said antigen of interest;

b) inducing, enhancing and/or maintaining expression of BCL6 in said B cell by providing said B cell with a nucleic acid molecule encoding BCL6 and/or STAT5, or a functional part or a functional derivative thereof, inducing, enhancing and/or maintaining expression of Blimp-1 in said B cell, preferably by providing said B cell with a nucleic acid molecule encoding STAT3, or a functional part or a functional derivative thereof or by culturing said B cell in the presence of IL-21, and inducing, enhancing and/or maintaining expression of a gene encoding an anti-apoptotic molecule of the BCL2 family, preferably Bcl-xL or Mcl-1, in said at least one B cell;

c) allowing expansion of said at least one B cell into a first B cell culture;

d) selecting at least one B cell from said first B cell culture with a binding avidity for said antigen of interest that is higher than the average binding avidity for said antigen of interest of B cells in said first B cell culture;

e) preferably allowing expansion of said at least one B cell selected in step d) into a second B cell culture;

f) determining the stability of antibodies produced by said at least one B cell selected in step d) or by said second B cell culture; and g) selecting at least one B cell capable of producing antibodies with a higher stability as compared to the average stability of antibodies produced by B cells of said first B cell culture.

Further provided is a method for selecting from an ex vivo B cell culture at least one B cell capable of producing antibodies with a higher stability as compared to the average stability of antibodies produced by said ex vivo B cell culture, the method comprising:

a) providing an ex vivo B cell culture capable of producing antibody specific for an antigen of interest;

b) selecting at least one B cell from said ex vivo B cell culture with a binding avidity for said antigen of interest that is higher than the average binding avidity of B cells of said ex vivo B cell culture for said antigen of interest;

c) determining the stability of antibodies produced by said at least one B cell selected in step b); and d) selecting at least one B cell capable of producing antibodies with a higher stability as compared to the average stability of antibodies produced by B cells of said ex vivo B cell culture, further comprising inducing, enhancing and/or maintaining expression of BCL6 in said ex vivo B cell culture by providing said ex vivo B cell culture with a nucleic acid molecule encoding BCL6 and/or STAT5, or a functional part or a functional derivative thereof, inducing, enhancing and/or maintaining expression of Blimp-1 in said ex vivo B cell culture, preferably by providing said ex vivo B cell culture with a nucleic acid molecule encoding STAT3, or a functional part or a functional derivative thereof or by culturing said ex vivo B cell culture in the presence of IL-21, and inducing, enhancing and/or maintaining expression of a gene encoding an anti-apoptotic molecule of the BCL2 family, preferably Bcl-xL or Mcl-1, in said ex vivo B cell culture.

A method according to the invention is preferably used for generating a cell line of B cells capable of producing stable antibodies that is stable for at least one week, preferably at least one month, more preferably at least three months, more preferably at least six months so that commercial production of antibodies with high stability has become possible. Preferably a stable cell line capable of producing monoclonal stable antibodies is produced. This is preferably performed by using memory B cells that have for instance been isolated from a sample by selection for CD19 (B cell marker) and cell surface IgG and/or CD27 (to mark memory cells). Furthermore, a memory B cell capable of specifically binding an antigen of interest is for instance selected in a binding assay using said antigen of interest. Subsequently, BCL6 and an anti-apoptotic nucleic acid, preferably Bcl-xL or Mcl-1, are preferably co-expressed in said B cell, resulting in a population of cells specific for said antigen of interest. Preferably only one memory B cell is used and expanded into an (ex vivo) B cell culture in a method as described herein, so that a B cell culture producing monoclonal antibodies (a monoclonal B cell line) is obtained.

In one embodiment, a B cell, preferably a memory B cell, that originates from an individual which had been previously exposed to an antigen of interest, is used in a method according to the invention. However, this is not necessary. It is also possible to use a B cell from an individual that has not been exposed to said antigen of interest. For instance, a B cell is used that is specific for another antigen but shows cross-reactivity with the antigen of interest. As another example, a B cell is used that is selected from a naïve B cell population of an individual. The naïve B cell population of an individual may contain B cells that show reactivity with an antigen of interest even though the individual has not been exposed to said antigen of interest. Such B cell from a naïve B cell population is for instance selected using labelled antigen of interest.

The invention further provides a method for producing antibodies specific for an antigen of interest, comprising:

selecting from an ex vivo B cell culture at least one B cell capable of producing antibody with a higher stability as compared to the average stability of antibodies produced by said ex vivo B cell culture with a method according to the invention;

culturing said at least one B cell into a B cell culture; and obtaining antibodies produced by said B cell culture.

Further provided is a method for producing antibodies specific for an antigen of interest, comprising:

selecting from an ex vivo B cell culture at least one B cell capable of producing antibody with a higher stability as compared to the average stability of antibodies produced by said ex vivo B cell culture with a method according to the invention;

optionally allowing expansion of said selected at least one B cell into a B cell culture;

determining the amino acid sequence of the heavy chain and/or light chain of said antibody with a higher stability; and expressing a nucleic acid molecule encoding the heavy chain and/or light chain of said antibody in a second cell. Said second cell is preferably a so-called producer cell, such as for instance a cell of a Chinese hamster ovary (CHO), NSO (a mouse myeloma) or 293(T) cell line, which are preferably adapted to commercial antibody production. Proliferation of such producer cells results in a producer cell line capable of producing stable antibodies according to the invention. Preferably, said producer cell line is suitable for producing antibodies for use in humans. Hence, said producer cell line is preferably free of pathogenic agents such as pathogenic micro-organisms.

Further provided is a method for identifying at least one mutation in the amino acid sequence of the heavy chain and/or light chain of an antibody as compared to the amino acid sequence of the heavy chain and/or light chain of a reference antibody, which mutation promotes stability of said antibody, comprising:

selecting from an ex vivo B cell culture at least one B cell capable of producing antibody with a higher stability as compared to the average stability of antibodies produced by said ex vivo B cell culture with a method according to the invention;

optionally allowing expansion of said selected at least one B cell into a B cell culture determining at least part of the amino acid sequence of the heavy chain and/or light chain of an antibody produced by said selected at least one B cell;

comparing said amino acid sequence with at least part of the amino acid sequence of the heavy chain and/or light chain of a reference antibody, thereby identifying at least one mutation in the amino acid sequence in the heavy chain and/or light chain of said antibody which mutation promotes stability of said antibody.

The amino acid sequence of at least part of the heavy chain and/or the light chain of an antibody selected in accordance with the invention or of an antibody produced by a B cell selected in accordance with the invention can be determined using any method known in the art, such as by mass spectrometry or Edman degradation reaction. Preferably the amino acid sequence of at least the complementarity determining regions (CDRs) of the heavy chain and/or light chain of the antibody are determined, more preferably the CDRs of the heavy chain and of the light chain.

A reference antibody is preferably an antibody produced by the first B cell culture or ex vivo B cell culture as referred to herein from which a B cell with a high binding avidity is selected in accordance with the invention. Hence, said reference antibody is preferably an antibody produced by a first B cell culture obtained in step c) of a method for producing a B cell capable of producing antibody for an antigen of interest in accordance with the invention. In another preferred embodiment, said reference antibody is an antibody produced by an ex vivo B cell culture capable of producing antibody specific for an antigen of interest provided in step a) of a method for selecting from an ex vivo B cell culture at least one B cell capable of producing antibodies with a higher stability as compared to the average stability of antibodies produced by said ex vivo B cell culture in accordance with the invention.

The invention furthermore provides isolated or recombinant B cells, B cell cultures and populations of B cells, preferably monoclonal B cell lines, obtained by a method according to the invention. Such B cells capable of producing stable antibodies are preferably stable for at least one week, preferably for at least one month, more preferably for at least three months, more preferably for at least six months, meaning that the B cell is capable of both replicating and producing antibody, or capable of replicating and developing into a cell that produces antibody, during said time periods. B cells selected or produced in accordance with the invention preferably comprise cells producing IgM, IgG, IgA, or IgE, preferably IgG. A B cell selected or produced in accordance with the invention is particularly suitable for use in producing an antibody producing B cell line. B cells capable of producing highly stable antibodies selected or produced in accordance with the invention are preferably cultured ex vivo and antibody is preferably collected for further use. Alternatively, the amino acid sequence of B cells capable of producing highly stable antibodies selected or produced in accordance with the invention is determined and a producer cell line is provided with a nucleic acid molecule encoding the heavy and/or light chain of the antibodies in order to produce and collect stable antibodies. Provided is therefore a method according to the invention further comprising determining at least part of the amino acid sequence of the heavy chain and/or light chain of said at least one B cell that is capable of producing antibodies with a higher stability. Antibodies obtained from a B cell or from a B cell culture or monoclonal B cell line selected and/or produced in accordance with the invention are also provided. Stable antibodies or functional parts thereof produced with a method according to the invention are useful for a wide variety of applications, such as for instance therapeutic, prophylactic and diagnostic applications, as well as research purposes and ex vivo experiments.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention is further explained in the following examples. These examples do not limit the scope of the invention, but merely serve to clarify the invention.

EXAMPLES

Generation and Characterization of Influenza Hemagglutinin B Cell Clone AT10_004

Human memory B cells were immortalized using the BCL6/Bcl-xL technology described by Kwakkenbos et al. (Nature medicine, 16(1), 123-128. doi:10.1038/nm 2071; Methods 2013 doi:10.1016/j.ymeth.2013.07.002; patent application WO 2007/067046). The identification and characterization of the cross-reactive anti-influenza Hemagglutinin specific B cell clone AT10_004 is described in patent applications WO 2013/081463 and WO 2012/072814. The binding of the AT10_004 antibody to the different Hemagglutinin proteins was tested using a solid phase ELISA or by using a FACS assay with virus infected cells (described in patent application WO 2013/081463). AT10_004 shows strong binding to most Group 2 Hemagglutinin proteins but only modest binding to Group 1 Hemagglutinin proteins is detected (Table 1).

TABLE 1

Binding of AT10_004 in ELISA or FACS-based assay to different influenza group 1 and group 2 Hemagglutinin (HA) subtypes.

| Influenza strain | Subtype | Group | Binding capacity |
|---|---|---|---|
| A/California/07/2009 | H1 | 1 | + |
| A/Netherlands/602/2009 | H1 | 1 | − |
| A/New Caledonia/20/1999 | H1 | 1 | + |
| A/Hawaii/31/2007 | H1 | 1 | + |
| A/Vietnam/1203/2004 | H5 | 1 | − |
| A/Turkey/Turkey/2004 | H5 | 1 | + |
| A/Hong Kong/1073/1999 | H9 | 1 | + |
| A/Aichi/2/1968 | H3 | 2 | ++ |
| A/Wyoming/03/2003 | H3 | 2 | ++ |
| A/Netherlands/177/2008 | H3 | 2 | ++ |
| A/Swine/St.Oedenrode/1996 | H3 | 2 | ++ |
| A/Swine/Ontario/01911-1/1999 | H4 | 2 | + |
| A/Chicken/Italy/1067/1999 | H7 | 2 | ++ |
| A/Netherlands/219/2003 | H7 | 2 | ++ |
| A/Chicken/Netherlands/621557/2003 | H7 | 2 | ++ |
| A/Duck/Hong Kong/786/1979 | H10 | 2 | − |
| A/Duck/AUS/341/1983 | H15 | 2 | + |

Selection of Subclones with Increased Antigen Binding

In patent application WO 2012/072814 it is shown that, within the heterogeneous subpopulation of a monoclonal B cell clone, cells with increased antigen binding capacity can be selected using a combination of antigen staining (H3-Alexa-647) and BCR staining BCR staining was performed with antibodies that bind to the heavy- or the light chain of the BCR. High H3 staining and equal or low BCR staining indicate higher antigen binding capacity of the BCR of that particular subclone, whereas low H3 staining and equal or high BCR staining indicates low antigen binding per BCR.

Figure 1:
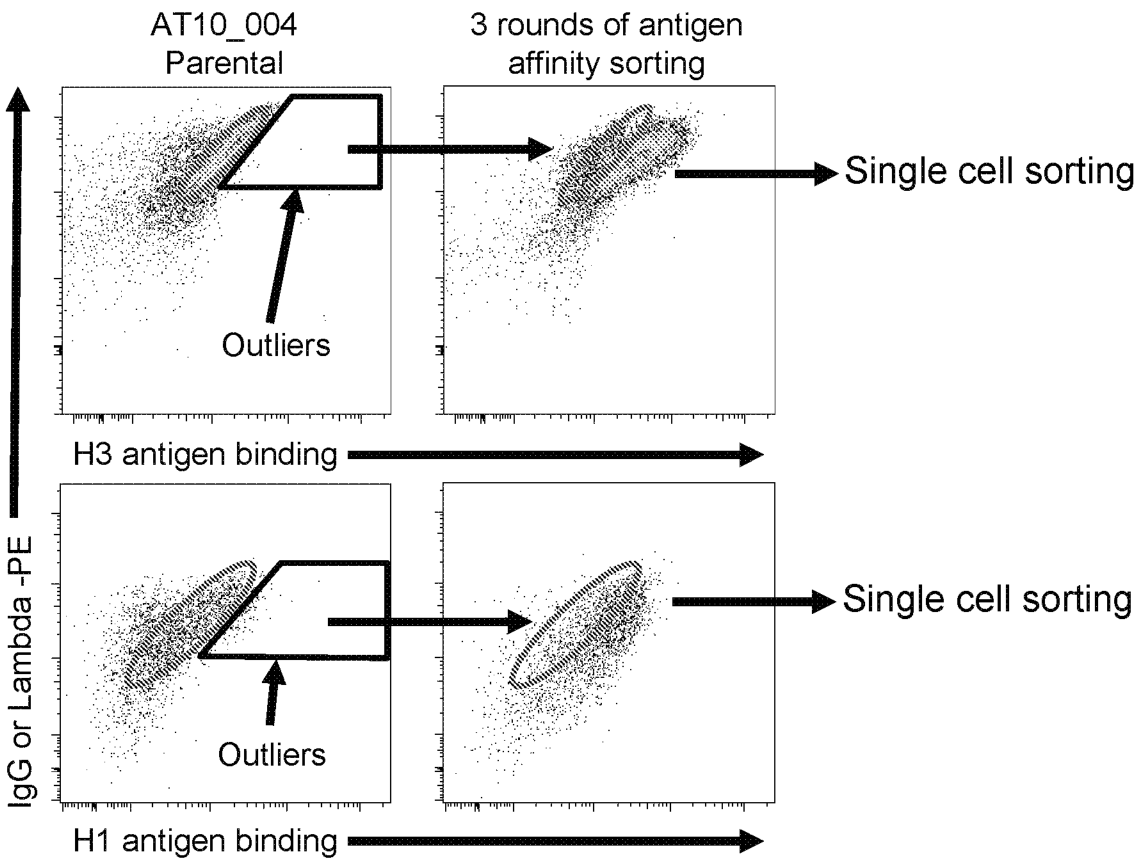
FIG. 1. Selection and isolation of subclones (outliers) with increased binding to labeled H1 or H3 compared to the average binding of the influenza group 1 and influenza group 2 cross reactive HA specific parental clone AT10_004. Cells were stained with Alexa-647 labeled HA H3- or H1 antigen together with IgG-PE or Lamda-PE antibody. Following three subsequent rounds of enrichment for increased antigen binding, AT10_004 cells single cell cloning was performed with a cell sorter.

In the present study, HA-specific B cell clone (AT10_004) was cultured for 2-3 weeks to produce millions of cells, creating an unbiased heterogeneous B cell population, before an antigen-BCR staining was performed. Cells that showed increased antigen binding to the soluble labeled HA protein of H1 or H3 (H1 HA: A/New Caledonia/20/1999 or H3 HA: A/Wyoming/03/2003) were selected and sorted on a cell sorter. After 3 rounds of sorting and growing, FACS analysis was performed on these cells to determine differences in antigen binding. Cells that were sorted three times for increased antigen binding show a clear shift in antigen staining compared to non-selected cells (FIG. 1). These sorted cells were then subjected to single cell cloning using a FACSAria III (BD Biosciences). The clones were cultured for 2-3 weeks to allow expansion and then tested for increased antigen binding compared to the parental clone.

Antigen Competition Assay

Figure 2:
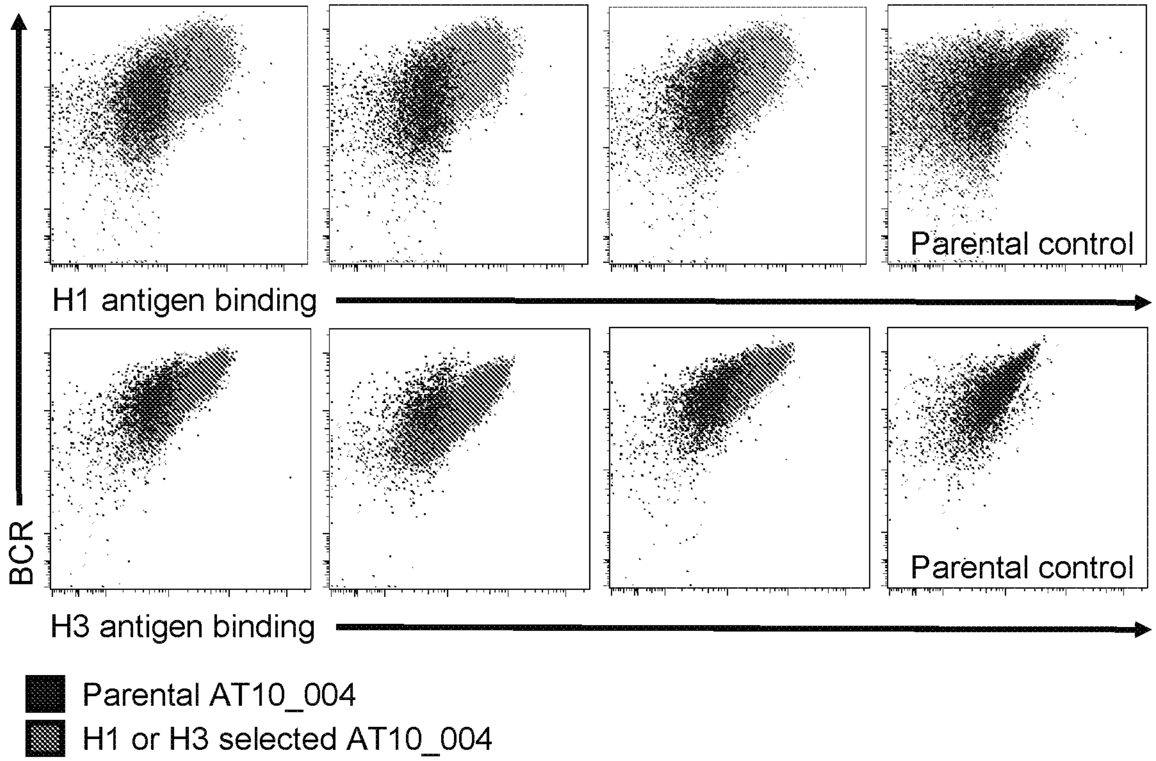
FIG. 2. Selection of subclones with increased H1 or H3 antigen binding compared to the parental AT10_004 clone. AT10_004 cells were labelled with a fluorescent CD19 antibody and mixed with non-labelled subclone cells. This mix of cells was stained with lambda-PE and Alexa-647 labelled H1 or H3. Shown is the intensity of antigen binding related to the BCR expression of the subclones compared to the parental AT10_004 cells.

Previously differences in antigen binding were detected by staining the exact same number of cells with BCR antibody and labeled antigen to have similar cell/staining solution-ratio. In the current experiments subclones that show increased antigen binding are detected using an antigen competition experiment. AT10_004 cells were harvested and stained with Pe-Cy7 labelled CD19 antibody on ice. After 15 minutes the cells were washed, seeded at 40.000 cells per well and 100 μl of subclone cells is added. Subsequently the cell mix is washed and stained with labelled antigen (H1 HA: A/New Caledonia/20/1999 or H3 HA: A/Wyoming/03/2003) and labelled BCR antibody. Cells are incubated for 1-3 hours on ice, washed and measured on a FACSCanto (BD Biosciences). The amount of labelled antigen binding to CD19 positive cells (the parental AT10_004 cells) is compared with the amount of labelled antigen bound to the subclone (CD19 negative). Plotted in FIG. 2 are 6 subclones that show increased antigen binding to either H1- or H3 antigen.

Cloning and Sequence Analysis of Selected Subclone Antibodies of AT10_004

A panel of subclones was selected based on enhanced antigen binding compared to the parental AT10_004 clone. Of these subclones we isolated total RNA with the RNeasy® mini kit (Qiagen), generated cDNA, performed PCR, and performed sequence analysis. To produce recombinant human IgG we cloned the heavy and light variable regions in frame with human IgG1 and Kappa constant regions into a pcDNA3.1 (Invitrogen) based vector and transiently transfected 293T cells. We purified recombinant IgG from the culture supernatant using MAbSelect Sure columns (GE Healthcare).

Sequence analysis of the selected AT10_004 subclones revealed that several of the subclones have identical mutations (Table 2), either as a single mutation or in combination with additional mutations. Interestingly, all of the subclones that show enhanced H3 binding have a mutated light chain. From the 17 H3 selected subclones, 11 have the light chain D50G mutation while the other 6 show the light chain S92Y mutation. All of the identified subclones (6) that show enhanced H1 binding contain the heavy chain P100dF mutation. Three of these subclones harbor a light chain mutation in addition. In the experiments described below we analyzed the effect of light chain S30N mutation detected in clone AT10_004.10.

TABLE 2

Description of the molecular characteristics of the subclones that were selected for increased antigen-binding capacity after 3 rounds of antigen specific sorting. From these subclones, recombinant antibodies were produced. Mut HC and Mut LC indicate mutations in the heavy or light chain respectively. Amino acid numering according to Kabat.

| | Selection | Mut HC | Mut LC | Location | Frequency |
|---|---|---|---|---|---|
| AT10-004 | — | | | | |
| AT10-004.2 | H3 | | D50G | LC: CDR2 | 8 (17) |
| AT10-004.3 | H3 | | D50G, | LC: CDR2 | 3 (17) |
| | | | I58V | LC: FWR3 | |
| AT10-004.5 | H3 | | S92Y | LC: CDR3 | 3 (17) |
| AT10-004.6 | H3 | A52aV | | HC: CDR2 | 2 (17) |
| | | | S92Y | LC: CDR3 | |
| AT10-004.7 | H3 | D58E | | HC: CDR2 | 1 (17) |
| | | | S92Y | LC: CDR3 | |
| AT10-004.8 | H1 | P100dF | | HC: CDR3 | 1 (6) |
| AT10-004.9 | H1 | P100dF, | | HC: CDR3 | 2 (6) |
| | | T107S | | HC: FWR4 | |
| AT10-004.10 | H1 | A24T, | | HC: FWR1 | 1 (6) |
| | | A52aV, | | HC: CDR2 | |
| | | P100dF, | | HC: CDR3 | |
| | | T110I | | HC: FWR4 | |
| | | | S30N | LC: CDR1 | |

AT10_004 Stability Testing

Figure 3:
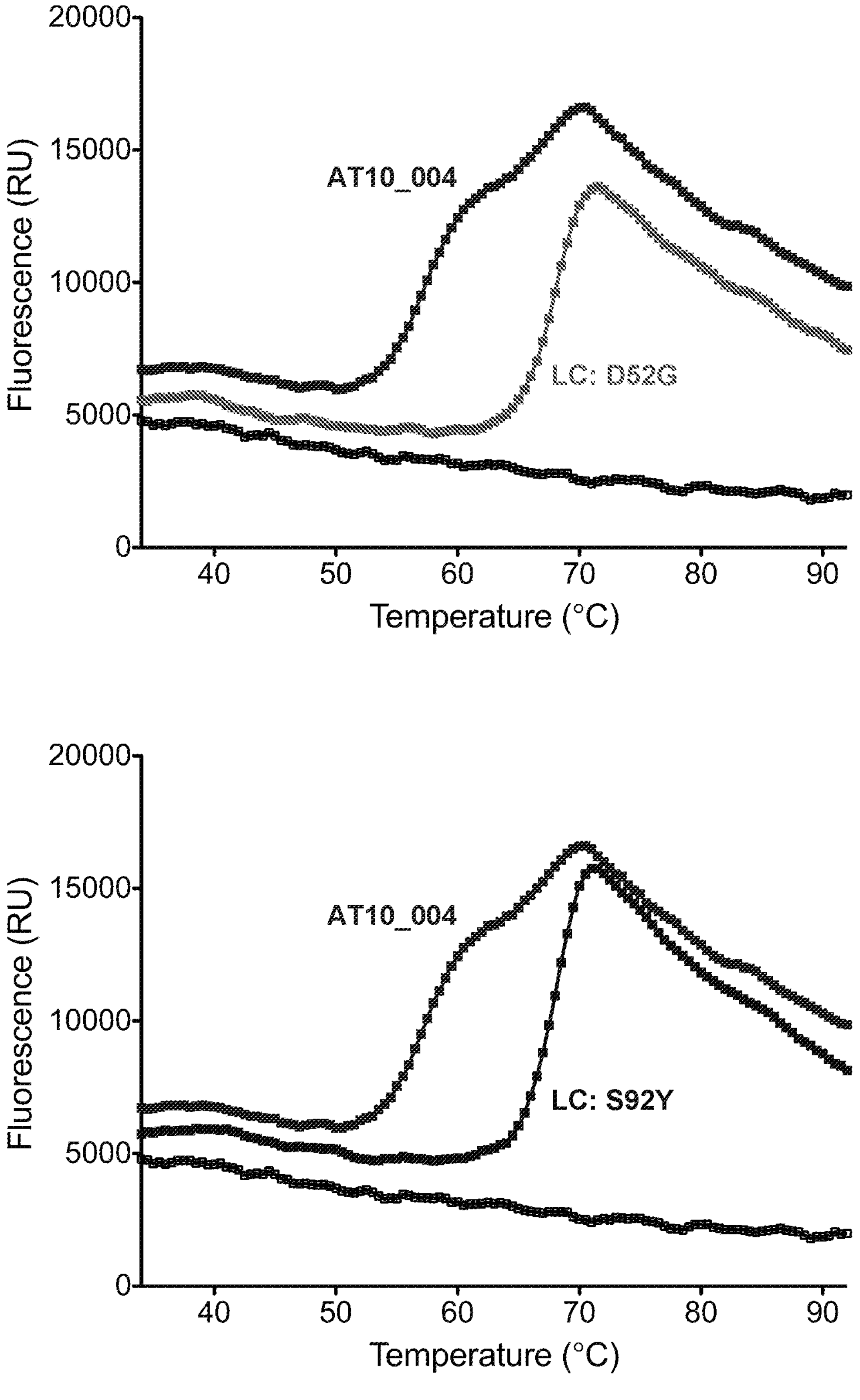
FIG. 3. Dynamic scanning fluorescence (DSF) melt curves of the recombinant parental and mutant AT10_004 antibodies. Whereas the parental AT10_004 shows a bimodal melt curve, the subclones with the light chain mutations (S30N (not shown), D50G and S92Y) show a single peak at high temperature only. The P100dF mutation does not influence the DSF curve.

We tested the structural stability of the recombinant parental and mutant AT10_004 antibodies with dynamic scanning fluorescence (DSF) (Phillips and Hernandez de la Pena, 2001, The Combined Use of the Thermofluor Assay and ThermoQ Analytical Software for the Determination of Protein Stability and Buffer Optimization as an Aid in Protein Crystallization. Hoboken, N.J., USA: John Wiley & Sons, Inc. doi:10.1002/0471142727.mb1028s94), using an iCycler RealTime PCR instrument (BIORAD) (FIG. 3). In the DSF assay, antibodies are subjected to increasing temperature, causing their structure to unfold. Protein unfolding is measured with a fluorescent reporter dye (SyPro, Invitrogen). The DSF meltcurve of the original AT10_004 antibody shows a multimodal pattern, representing the unfolding of the antibody subdomains (Fab, $CH_2$ and $CH_3$) at different temperatures (Garber and Demarest, 2007, Biochemical and Biophysical Research Communications, 355, 751-757). Mutants containing the light chain mutations S30N (not shown), D50G and S92Y lack the first "unfolding peak" at ±60° C. observed in the parental antibody (FIG. 3), indicating that these selected mutants have an increased thermostability.

Figure 4A:
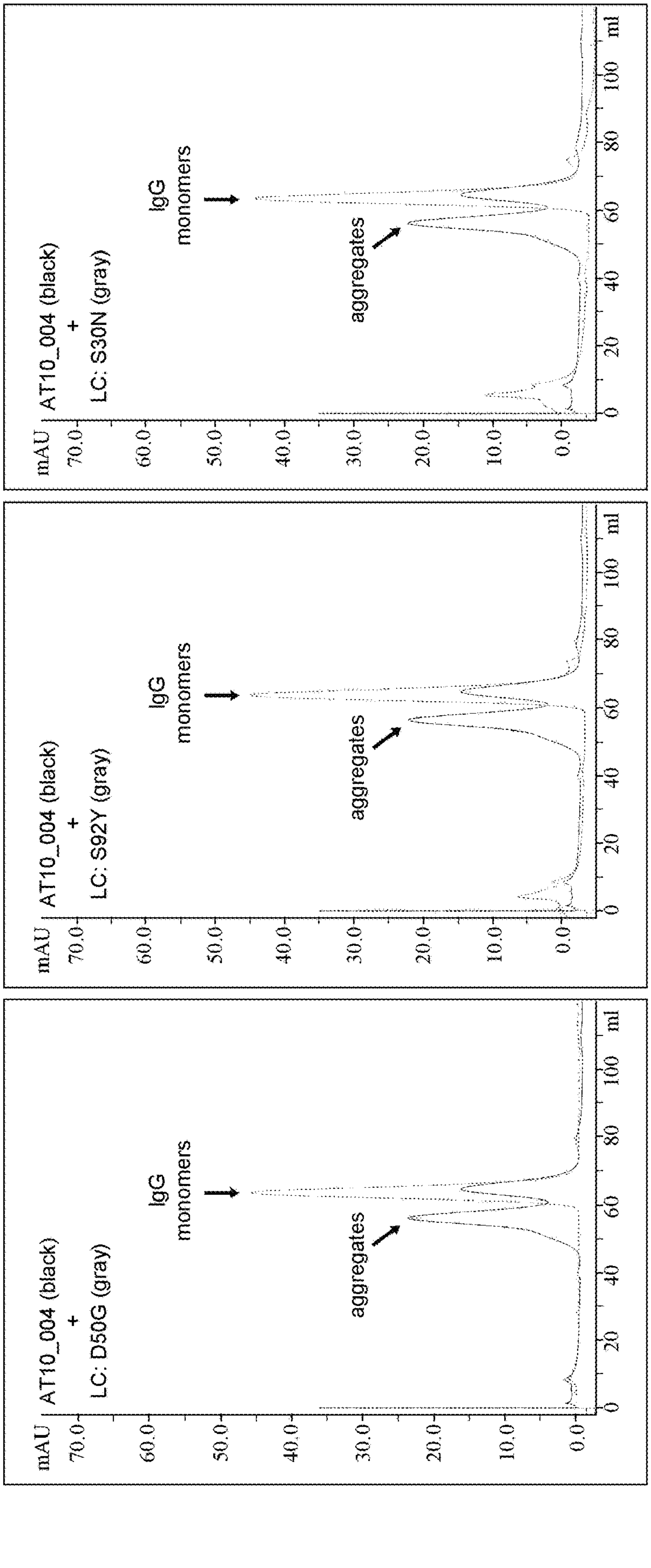
FIG. 4. A). Gel filtration chromatogram overlays of recombinant parental and mutant AT10_004. Recombinant AT10_004 antibody solutions were applied on to a gel filtration column to detect the presence of aggregated antibodies. B) Antibody monomers of AT10_004 and LC mutant D50G were purified using gel filtration (panel 1 and 3) and stored at −20° C. After 2 months antibody solutions were thawed and analyzed for the presence of antibody aggregates (panel 2 and 4).
Figure 4B:
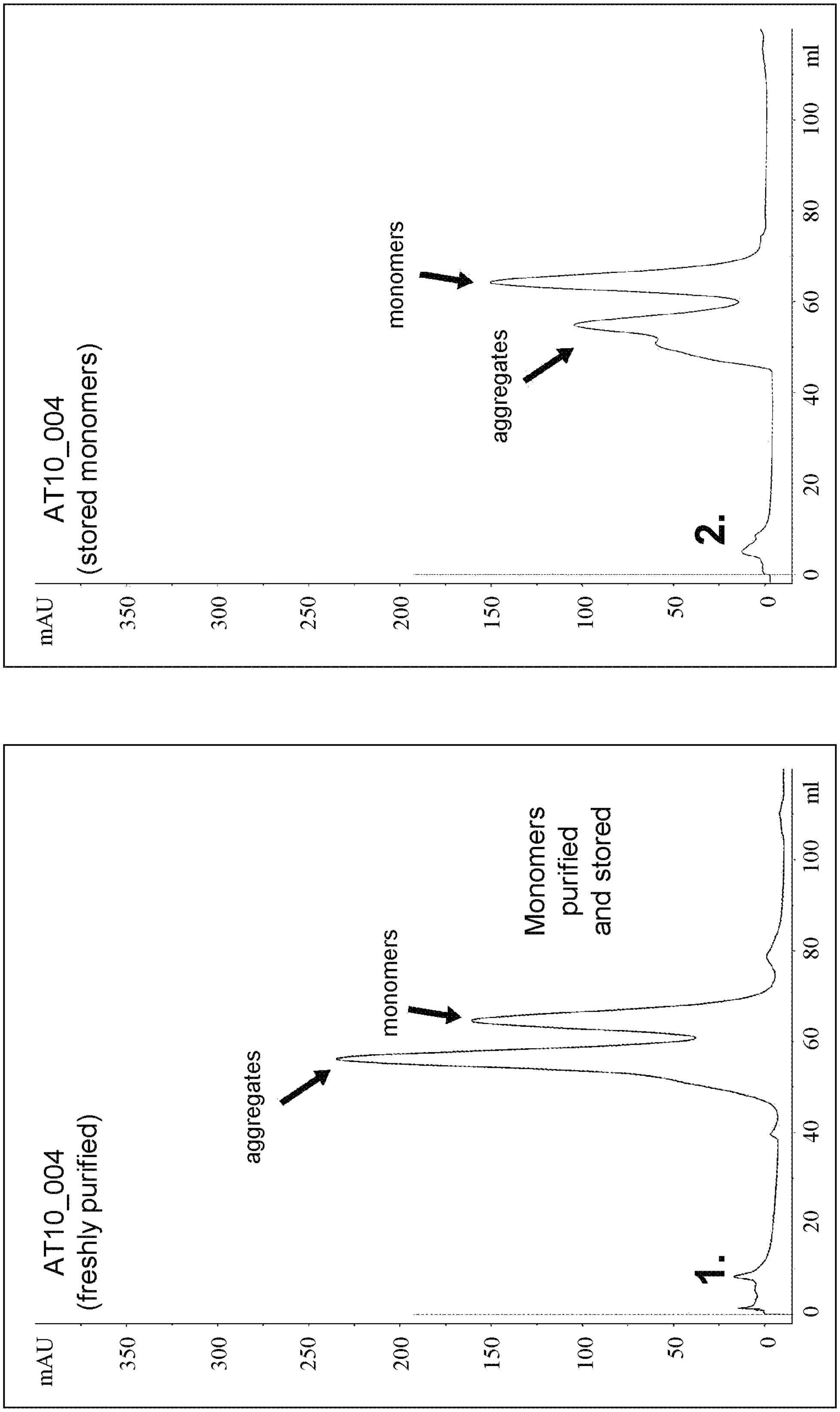

Next, we analyzed the presence of aggregates in the recombinantly produced, purified antibody solutions by gel filtration, on a Superdex200 gel filtration column (GE Healthcare). The gel filtration analysis clearly shows that aggregates are present in purified AT10_004 (FIG. 4*a*). AT10_004 mutants with a light chain mutation (S30N, D50G or S92Y) do not form these aggregates (FIG. 4*a*). We further analyzed the effect of light chain mutations on the stability of AT10_004 by looking at formation of aggregates during long-term storage. Antibody monomers (AT10_004 and mutant LC: D50G) were purified with gel filtration (FIG. 4*b*, panel 1 and 3) and stored for two months at −20° C. After storage, the amount of aggregates in each sample was determined with gel filtration. AT10_004 contains more aggregates than mutant LC: D50G (FIG. 4*b*, panel 2 and 4). Similar results are obtained with light chain mutants S30N and S92Y (data not shown).

These results suggest that the light chain mutations (S30N, D50G and S92Y) we have obtained enhance the thermostability of the AT10_004 antibody and that the mutations prevent formation of aggregates.

Virus Neutralization

Figure 5:
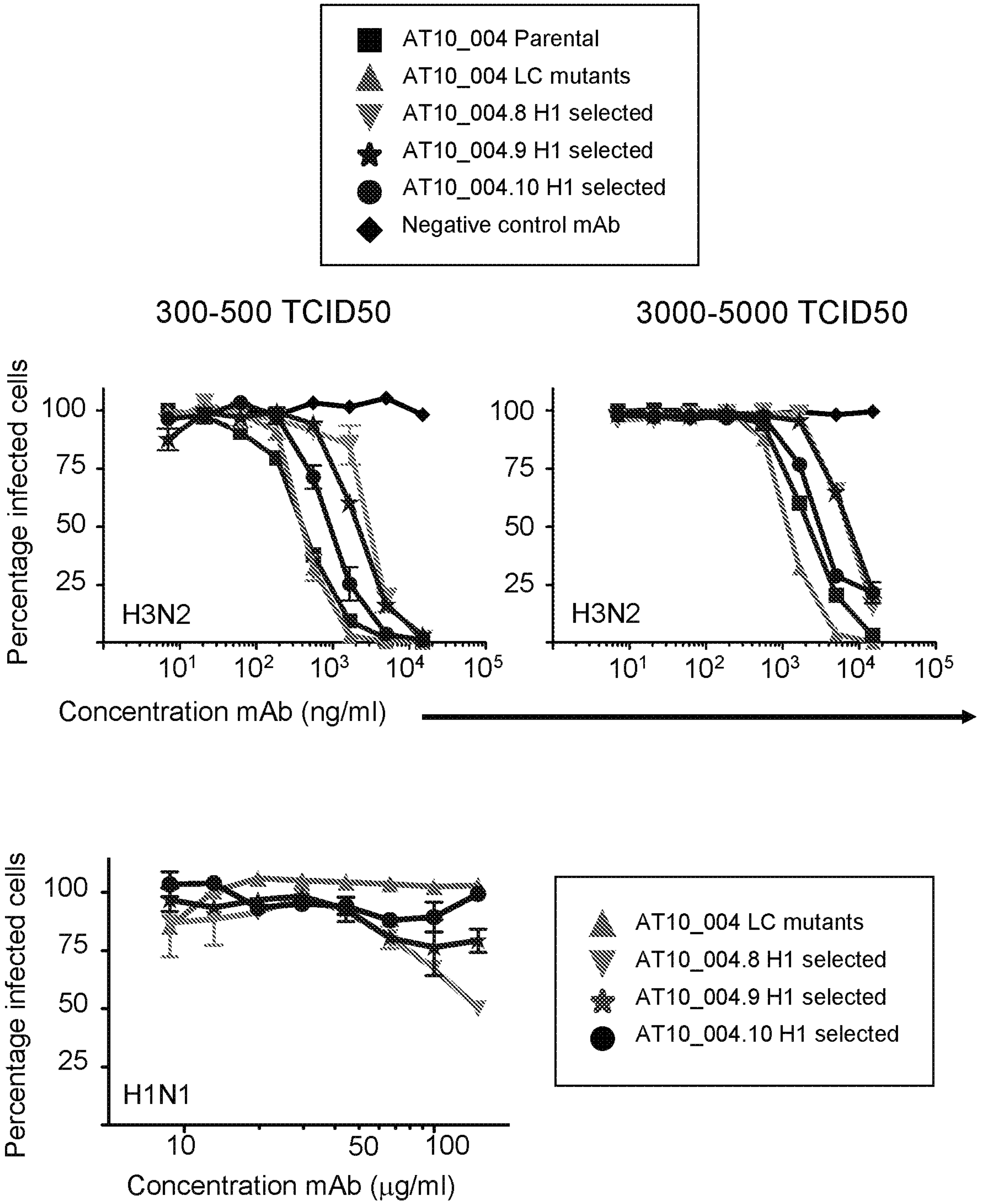
FIG. 5. In vitro influenza A virus neutralization of H1N1 (A/Hawaii/31/2007) and H3N2 (A/Netherlands/177/2008) virus on MDCK-SIAT cells by recombinant antibodies. Top panels show H3N2 neutralization using low (left panel) or high (right panel) viral titers. Bottom panel shows the neutralization of H1N1 virus by the different (mutant) antibodies.

To determine whether the obtained mutant antibodies had different neutralizing capacities compared to the parental AT10_004 antibody, an in vitro neutralization assay was performed. The assay was performed on MDCK-SIAT cells (Matrosovich M. et al., 2010, Journal of Virology, 77(15), 8418-8425). MDCK-SIAT cells were grown in DMEM/8% FCS/PS/G418 in a 96 well plate (CellCarrier Plate, PerkinElmer) to 80-100% confluency. Neutralization assays are performed in Optimem/PS/G418/Trypsin medium without FCS or BSA. Fifty µl of recombinant mAb was mixed with 50 µl of virus suspension (100TCID50/50 µl or 1000TCID50/50 µl) of H3N2 (A/Ned/177/2008) or H1N1 (A/Hawaii/31/2007) Influenza and incubated for 1 h at 37° C. The suspension was then transferred in multiply into 96-well plates containing MDCK-SIAT cells in 100 µl Optimem/PS/G418/Trypsin. Prior to use the MDCK-SIAT cells were washed twice with 150 µl PBS. The plates were then centrifuged for 15 minutes at RT at 2500 rpm and placed at 37° C./5% CO2. After 24 h cells were washed twice with PBS, fixed with Formalin (37% formaldehyde in water) for 10 minutes at RT, washed twice with 150 µl PBS and stained with DAPI and an antibody against the nuclear protein of the Influenza virus (NP-FITC, Abcam) at RT. After 30 minutes cells were washed twice with 150 µl PBS and 100 µl of PBS+50% glycerol was added to the wells. Viral infection of the MDCK-SIAT cells was measured and analyzed on the Operetta (PerkinElmer) using a 10× objective. To quantify neutralizing capacity of the mAbs the number of infected cells was counted (positive for DAPI and NP-FITC). IC50 values were calculated with Prism (GraphPad software). Antibodies containing the LC: D50G or LC: S92Y mutation maintained H3N2 neutralizing capacity at low TCID50 and even have increased neutralizing capacity as evidenced by a lower IC50 when the neutralization assay was performed with a higher viral dose (>3000TCID50) (FIG. 5 and Table 3). No increase in H1 neutralizing capacity for these light chain mutants was detected (tested up to 150 µg/ml). The AT10_004 subclones that were identified by selection with labeled H1 antigen (AT10_004.8, AT10_004.9 and AT10_004.10) showed reduced H3N2 neutralizing capacity (FIG. 5 and Table 3) however, AT10_004.8 and AT10_004.9 showed increased H1N1 neutralizing potency. Whereas the original AT10_004 antibody or the light chain mutants show no inhibition of H1N1 infection antibody, AT10_004.8 shows a marked effect on H1N1 infection.

TABLE 3

IC50 values for H3 neutralization of recombinant AT10_004 antibody and the different recombinant antibody subclones of AT10_004 at two virus concentrations.

| Clone | Selection | Mut HC | Mut LC | IC50 H3[(1)] (ng/ml) | IC50 H3[(2)] (ng/ml) |
|---|---|---|---|---|---|
| 004 | — | | | 436 | 2163 |
| 004.2 | H3 | | D50G | 433 | 1230 |
| 004.5 | H3 | | S92Y | 424 | 1028 |
| 004.8 | H1 | P100dF | | 3127 | 5174 |
| 004.9 | H1 | P100dF, T107S | | 2118 | 5732 |

TABLE 3-continued

IC50 values for H3 neutralization of recombinant AT10_004 antibody and the different recombinant antibody subclones of AT10_004 at two virus concentrations.

| Clone | Selection | Mut HC | Mut LC | IC50 H3[(1)] (ng/ml) | IC50 H3[(2)] (ng/ml) |
|---|---|---|---|---|---|
| 004.10 | H1 | A24T, A52aV, P100dF, T110I | S30N | 922 | 2328 |

[(1)]300-500 TCID50

[(2)]3000-5000 TCID50

Surface Plasmon Resonance (SPR) Analysis

SPR analysis was performed on an IBIS MX96 SPR imaging system (IBIS Technologies BV, Enschede, The Netherlands) as described before (Lokate et al., 2007, J Am Chem Soc. 129(45):14013-8). In this experiment, antibodies (1.0 μg/ml in coupling buffer: 10 mM MES-NaOH, pH 4.5+0.05% Tween20) were directly immobilized on an Easy2Spot gold-film gel-type SPR-sensor (Ssens, Enschede, The Netherlands) using a continuous flow microspotter device (Wasatch Microfluidics, Salt Lake City, Utah, USA). After spotting, the sensor was de-activated with 50 mM ethanolamine, pH 8.5. After de-activation, several blank injections cycles were done, each consisting of 45 minutes injection with empty assay buffer (PBS+0.05% sodium azide, 0.05% Tween20 and 0.01% BSA) followed by 2 minutes incubation with regeneration buffer (50 mM glycine-HCl, pH 2.0).

Figure 6:
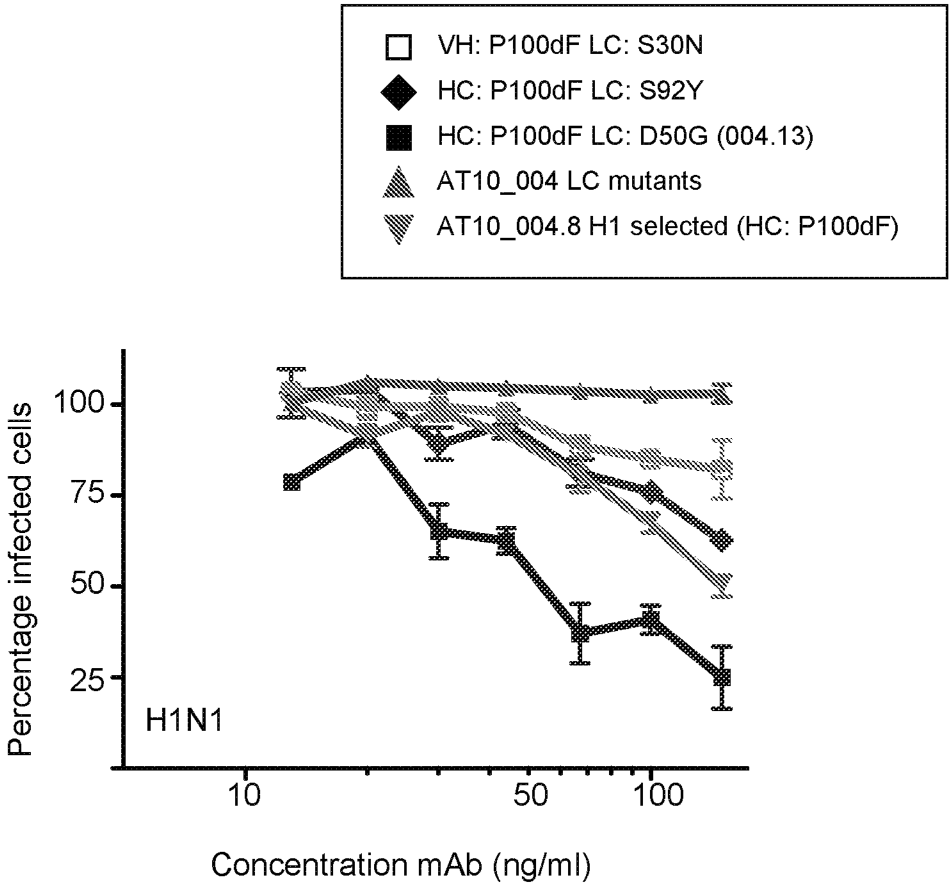
FIG. 6. In vitro influenza A virus neutralization of H1N1 (A/Hawaii/31/2007) virus on MDCK-SIAT cells with stabilized recombinant AT10_004.8 (HC: P100dF) mutant antibodies.

The SPR analysis consisted of multiple cycles of concatenated injections with H3 or H1 proteins. Each cycle consisted of an association step (10 min), in which recombinant influenza HA3- or H1-proteins (H1 HA: A/California/07/09; H3 HA: A/Wyoming/03/2003), diluted in assay buffer, are injected on the coated sensor; a dissociation step (15 min), in which the sensor is flushed with assay buffer, and, lastly, a wash with regeneration buffer (2 min), to remove any remaining bound analyte from the sensor. SPR data was analyzed using Sprint software (version 1.6.8.0, IBIS Technologies BV, Enschede, The Netherlands). Binding constants were fitted using Scrubber2 software (Biologic Software, Campbell, Australia). Subclones with a stabilizing mutation in the light chain (clones AT10_004.2 (D50G), AT10_004.5 (S92Y) & AT10_004.12 (S30N)) all have an H3 affinity similar as the original AT10_004 clone (Table 4). The H1-affinity of these subclones is also similar to the original AT10_004 clone (no more then 50% deviation) (Table 4). The H1-induced HC: P100dF mutation increases binding affinity to H1 and reduces H3-binding (Table 4); this corresponds to the neutralizing capacity of this subclone (AT10_004.8) for these viruses. When subclone AT10_004.8 (P100dF) is stabilized by incorporating one of the stabilizing LC mutations we have identified, its affinity for H1 increases further (Table 4); this is most evident for mutant AT10_004.13 (LC: D50G). This mutant (HC: P100dF+LC: D50G) also shows an improved neutralizing capacity for H1, compared to the HC: P100dF mutation alone (FIG. 6).

TABLE 4

SPR analysis of the binding of recombinant AT10_004 and AT10_004 subclones to recombinant H1 and H3 HA.

| Clone | Selection | Mut HC | Mut LC | Affinity ($K_D$) H1 (pM) | Affinity ($K_D$) H3 (pM) |
|---|---|---|---|---|---|
| 004 | — | | | 660 (±100) | 39 (±4) |
| 004.2 | H3 | | D50G | 970 (±130) | 35 (±1) |
| 004.5 | H3 | | S92Y | 490 (±10) | 34 (±3) |
| 004.8 | H1 | P100dF | | 240 (±90) | 150 (±60) |
| 004.12 | | | S30N | 540 (±70) | 32 (±1) |
| 004.13 | | P100dF | D50G | 28 (±2) | 100 (±40) |
| 004.14 | | P100dF | S92Y | 110 (±40) | 34 (±2) |
| 004.15 | | P100dF | S30N | 41 (±20) | 29 (±1) |

What is claimed is:

1. A method for producing a B cell having a high avidity for an antigen of interest comprising:

a) selecting at least one B cell capable of producing said antibody specific for said antigen of interest or at least one B cell capable of developing into a B cell capable of producing said antibody specific for said antigen of interest;

b) inducing, enhancing and/or maintaining expression of BCL6 and inducing, enhancing and/or maintaining expression of an anti-apoptotic nucleic acid in said at least one B cell;

c) allowing expansion of said at least one B cell into a first B cell culture;

d) selecting at least one B cell from said first B cell culture with a binding avidity for said antigen of interest that is higher than the average binding avidity for said antigen of interest of B cells in said first B cell culture;

e) optionally allowing expansion of said at least one B cell selected in step d) into a second B cell culture;

f) determining the stability of antibodies produced by said at least one B cell selected in step d) or by said second B cell culture;

g) determining affinity for said antigen of interest of said antibodies produced by said at least one B cell selected in step d) or by said second B cell culture; and h) selecting at least one B cell, wherein said selected B cell is capable of producing antibodies with a higher stability as compared to the average stability of antibodies produced by B cells of said first B cell culture; wherein said selected B Cell exhibits affinity for said antigen of interest that is the same as, or less than, the average affinity for said antigen of interest of antibodies produced by said first B cell culture; and wherein said selected B cell is capable of producing antibodies that exhibit(s) affinity for said antigen of interest that is the same as, or less than, the average affinity for said antigen of interest of antibodies produced by said first B cell culture.

2. The method according to claim 1, wherein allowing expansion of said at least one B cell into said B cell culture and selecting at least one B cell from said B cell culture capable of producing antibody with a binding avidity for said antigen of interest that is higher than the average binding avidity of B cell receptors or antibodies produced by said B cell culture for said antigen of interest in step d are repeated at least once.

3. The method according to claim 1, further comprising determining at least part of the amino acid sequence of the heavy chain and/or light chain of said at least one B cell that is capable of producing antibodies with a higher stability.

4. The method according to claim 1 wherein the stability of antibodies produced by said at least one B cell selected as having a binding avidity higher than the average binding avidity of B cells in said first B cell culture or the stability of antibodies produced by said second B cell culture is determined within four months, from selecting said at least one B cell having a binding avidity higher than the average binding avidity of B cells in said first B cell culture.

5. The method according to claim 1 further comprising directly or indirectly inducing, enhancing and/or maintaining the amount of Blimp 1 expression product in said at least one B cell.

6. The method according to claim 1, wherein said at least one B cell originates from an individual which had been previously exposed to said antigen of interest.

7. The method according claim 1, wherein said first B cell culture is a monoclonal B cell culture.

8. The method according to claim 1 wherein the stability of antibodies produced by said at least one B cell selected as having a binding avidity higher than the average binding avidity of B cells in said first B cell culture or the stability of antibodies produced by said second B cell culture is determined within one month, from selecting said at least one B cell having a binding avidity higher than the average binding avidity of B cells in said first B cell culture.

9. The method according to claim 1, wherein said anti-apoptotic nucleic acid comprises a gene encoding anti-apoptotic molecules of the BCL2 family.

10. The method according to claim 1, wherein said anti-apoptotic nucleic acid comprises a gene encoding Bcl-xL, or Mcl 1, or a functional part thereof.

* * * * *